United States Patent
Le Gros

(10) Patent No.: US 9,913,896 B2
(45) Date of Patent: Mar. 13, 2018

(54) ATTENUATED PARVOVIRUS VACCINE FOR MUSCOVY DUCK PARVOVIRUS AND GOOSE PARVOVIRUS (DERZSY'S DISEASE)

(71) Applicant: Merial, Inc., Duluth, GA (US)

(72) Inventor: Francois Xavier Le Gros, Saint Genis Laval (FR)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 15/378,147

(22) Filed: Dec. 14, 2016

(65) Prior Publication Data

US 2017/0173146 A1 Jun. 22, 2017

Related U.S. Application Data

(62) Division of application No. 14/427,197, filed on Mar. 10, 2015, now Pat. No. 9,555,098.

(60) Provisional application No. 61/698,842, filed on Sep. 10, 2012.

(51) Int. Cl.
*A61K 39/23* (2006.01)
*C12N 7/00* (2006.01)
*C07K 14/005* (2006.01)
*A61K 39/00* (2006.01)

(52) U.S. Cl.
CPC ............ *A61K 39/23* (2013.01); *C07K 14/005* (2013.01); *C12N 7/00* (2013.01); *A61K 2039/5254* (2013.01); *A61K 2039/552* (2013.01); *C12N 2750/14122* (2013.01); *C12N 2750/14134* (2013.01); *C12N 2750/14322* (2013.01); *C12N 2750/14334* (2013.01)

(58) Field of Classification Search
None
See application file for complete search history.

(56) References Cited

U.S. PATENT DOCUMENTS

2004/0208886 A1 10/2004 Daeffler et al.

OTHER PUBLICATIONS

Gough Re et al., 1982, "Studies with a duck embryo adapted goose parvovirus vaccine", Avian Pathology, 11(3):503-510.
Wozniakowski Grzegore et al., 2009, "Genetic variacne of Derzsy's disease strains isolated in Poland", J. of Molecular and Genetic Medicine, vol. 3(2), 210-216.
Le Gall-Recule Ghislaine et al., 1996, "Expression of muscovy duck parvovirus capsid proteins (Vp2 and VP3) in a baculovirus expression system and demonstration of immunigy induced by the recombinant proteins", J of General Virology, vol. 77(9), 2159-2163.
Lee et al., 2010, "CpG oligodeoxynucleotides containing GACGTT motifs enhance the immune responses elicited by a goose parvovirus vaccine in ducks", Vaccine, vol. 28, 7956-7962.

*Primary Examiner* — Benjamin P Blumel
(74) *Attorney, Agent, or Firm* — Judy Jarecki-Black; Ruoying Chen; Merial Inc.

(57) ABSTRACT

This disclosure provides an attenuated palmiped parvovirus that affords heterologous protection for both Muscovy duck parvovirus and goose parvovirus (i.e., Derzsy's Disease). The disclosure further provides compositions comprising the same, and methods of production and use thereof.

3 Claims, 10 Drawing Sheets

Figure 2. Clinical scores, D0 to D21
☐1 (locomotor problems) ☐2 (lameness) ▩3 (paresis) ■4 (death)

Figure 3 Bodyweights at D21

FIG. 4a
FIG. 4b
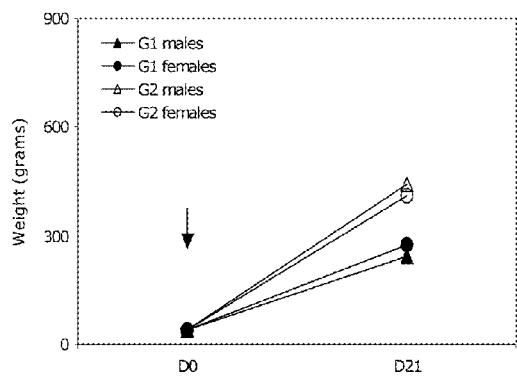
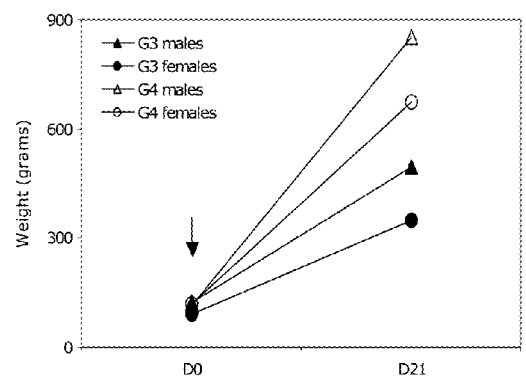
FIG. 5
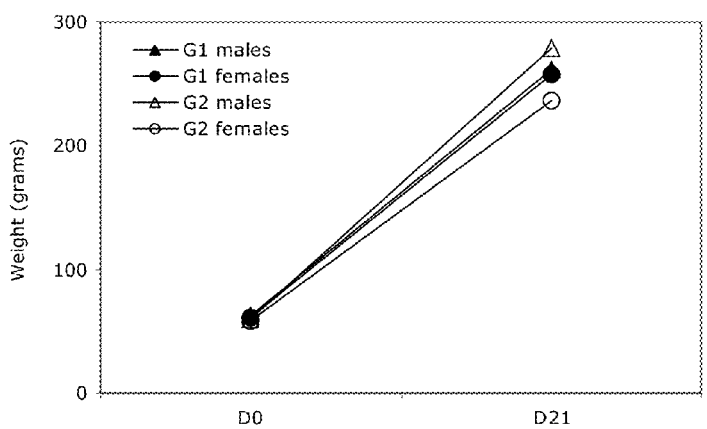

FIG. 12A

```
VP1 Palmivax   (1)   ATGTCTACTTTTTTAGATTCTTTTGAAGAGTGGTATGAGACTGCAGCCGC
VP1 Parvoduck  (1)   ATGTCTAATTTTTTAGAGGAATTTGAAGACTGGTATGAGACTGCAGCCGC VP1 Palmivax   (51)  CTCGTGGCGGAATCTGAAAGCTGGAGCCCCTCAGCCAAAACCAAACCAGC
VP1 Parvoduck  (51)  ATCTTGGCGGCATTTGAAAGCTGGAGCCCCCAAGCCAAAATCAAACCAGC VP1 Palmivax   (101) AGTCTCAGTCTGTGTCTCCAGACAGAGAACCCGAAGGAAAAGATAATAAT
VP1 Parvoduck  (101) AATCTCAGTCTGTGTCTACAGACAGAAAACCTCAACGAAAAGACAATAAT VP1 Palmivax   (151) CGGGGCTTTGTACTTCCTGGCTATAAGTATCTTGGGCCTGGTAACGGTCT
VP1 Parvoduck  (151) AGGGGCTTTGTACTTCCTGGCTATAAGTATCTTGGGCCTGGTAACGGCCT VP1 Palmivax   (201) TGATAAAGGCCCACCTGTCAATAAGGCGGACAACGTCGCGCTTGAACACG
VP1 Parvoduck  (201) TGATAAAGGGCCACCTGTCAATAAAGCGGACAACGTCGCGCTTGAGCACG VP1 Palmivax   (251) ACAAGGCCTACGACCTACAGCTTAAAGCGGGAGACAATCCATATATAAAA
VP1 Parvoduck  (251) ATAAAGCGTACGACCAGCAGCTCAAGGCAGGAGACAACCCCTATATAAAA VP1 Palmivax   (301) TTCAATCACGCTGACCAGGACTTTATAGATAGCCTCCAAGACGACCACTC
VP1 Parvoduck  (301) TTTAATCACGCAGATCAAGAATTTATAGATAATCTGCAAGGTGATACCTC VP1 Palmivax   (351) ATTTGGAGGTAATCTTGGAAAGGCTGTATTCCAGGCCAAAAAACGTATCT
VP1 Parvoduck  (351) CTTTGGAGGCAACCTCGGAAAAGCCGTATTCCAAGCTAAAAAAGAATTC VP1 Palmivax   (401) TAGAGCCATTCGGCCTAGTAGAAGAGCCTATCAACACGGCACCTGCAAAA
VP1 Parvoduck  (401) TAGAGCCTTTAGGCCTAGTAGAAGAACCTGTAAACACGGCTCCTGCTAAA VP1 Palmivax   (451) AAAAATACAGGGAAGCTTACTGACCATTACCCAGTAGTTAAGAAGCCTAA
VP1 Parvoduck  (451) AAGAGTAGTGGAAAACTAACAGATCACTACCCTATAGTAAAGAAGCCTAA VP1 Palmivax   (501) ACTCACCGAGGAAGTCAGTGCGGGAGGTGGTAGCAGTGCCGTACAAGACG
VP1 Parvoduck  (501) ATTATCTGAACAAAACTCTCCTTCACGTAGTAATAGTGGAGGAGAACCAA VP1 Palmivax   (551) GAGGAGCCACCGCGGAGGGCACCGAACCTGTGGCAGCATCTGAAATGGCA
VP1 Parvoduck  (551) GTGCAGCTGCCACCGAAGGCTCCGAACCTGTGGCAGCACCTAACATGGCA VP1 Palmivax   (601) GAGGGAGGAGGCGGAGCTATGGGCGACTCTTCAGGGGGTGCCGATGGAGT
VP1 Parvoduck  (601) GAGGGAGGAAGCGGAGCTATGGGCGACTCTGCAGGGGGTGCCGATGGACT VP1 Palmivax   (651) GGGTAATGCCTCGGGAAATTGGCATTGCGATTCCCAATGGATGGGAAACA
VP1 Parvoduck  (651) GGGTAATGCCTCAGGAAATTGGCATTGCGATTCCCAATGGCTGGGAGACA VP1 Palmivax   (701) CAGTCATCACAAAGACCACCAGAACCTGGGTCCTGCCAAGCTACAACAAT
VP1 Parvoduck  (701) CAGTCATTACCAAGACTACAAGAACCTGGGTCCTGCCAAGCTACAACAAC VP1 Palmivax   (751) CACATCTACAAAGCAATTACCAGTGGAACCTCTCAAGATGCAAATGTCCA
VP1 Parvoduck  (751) CACATCTACAAAGCCATCACAAGCGGAACAAACCCAGACTCAAATACCCA VP1 Palmivax   (801) GTATGCTGGATACAGTACCCCCTGGGGGTACTTTGATTTCAATCGCTTCC
VP1 Parvoduck  (801) ATATGCTGGATACAGCACCCCCTGGGGGTACTTTGATTTCAACAGATTCC VP1 Palmivax   (851) ACTGCCACTTCTCCCCTAGAGACTGGCAGAGACTTATCAACAACCACTGG
VP1 Parvoduck  (851) ACTGCCATTTCTCTCCAAGAGACTGGCAGAGACTCATCAACAACCATTGG
```

FIG. 12B

```
VP1 Palmivax   (901)  GGAATCAGGCCCAAGTCTCTTAAATTCAAGATCTTCAATGTTCAAGTCAA
VP1 Parvoduck  (901)  GGGATTAGACCGAAAGCACTCAAATTCAAGATATTCAATGTGCAAGTTAA VP1 Palmivax   (951)  GGAAGTCACAACGCAGGATCAGACAAAGACCATTGCAAACAATCTCACCT
VP1 Parvoduck  (951)  AGAAGTTACGACGCAAGACCAGACAAAGACTATTGCTAACAACCTTACCT VP1 Palmivax  (1001)  CAACAATTCAAGTTTTTACGGATGATGAGCATCAACTCCCGTATGTCCTG
VP1 Parvoduck (1001)  CTACAATCCAGATATTCACGGATAATGAACACCAGCTGCCCTATGTTCTG VP1 Palmivax  (1051)  GGCTCGGCTACGGAAGGGACCATGCCGCCGTTCCCGTCGGATGTCTATGC
VP1 Parvoduck (1051)  GGCTCGGCCACGGAGGGGACGATGCCACCGTTCCCCTCAGATGTGTATGC VP1 Palmivax  (1101)  CCTGCCGCAGTACGGGTACTGCACAATGCACACCAACCAGAATGGAGCAC
VP1 Parvoduck (1101)  CTTGCCCCAGTACGGCTACTGCACAATGCACACCAACCAGAGTGGAGCGA VP1 Palmivax  (1151)  GGTTCAATGACCGTAGTGCATTCTACTGCTTAGAGTACTTCCCTAGTCAG
VP1 Parvoduck (1151)  GATTCAATGACAGAAGTGCCTTCTATTGCTTAGAGTACTTCCCCAGTCAG VP1 Palmivax  (1201)  ATGCTGAGAACAGGTAACAACTTTGAGTTCACATTTGACTTTGAAGAAGT
VP1 Parvoduck (1201)  ATGCTGAGAACAGGGAATAATTTTGAATTCAGTTTTGAGTTTGAAGAAGT VP1 Palmivax  (1251)  TCCTTTCCACAGCATGTTCGCTCATTCACAGGACTTAGACAGGCTTATGA
VP1 Parvoduck (1251)  TCCTTTCCATAGCATGTTCGCTCATTCACAGGATTTAGACAGGCTAATGA VP1 Palmivax  (1301)  ACCCCCTAGTGGATCAATACCTCTGGAATTTCAATGAGGTAGACAGCAGC
VP1 Parvoduck (1301)  ATCCTCTCCTAGATCAGTACCTGTGGAATTTCTCTGAGGTAATGGTGGC VP1 Palmivax  (1351)  AGAAATGCTCAATTTAAAAAAGCTGTGAAGGGGCTTATGGCACCATGGG
VP1 Parvoduck (1351)  AGGAATGCACAGTTCAAAAAAGCTGTGAAAGGAGCATTTGGTGCAATGGG VP1 Palmivax  (1401)  CCGCAATTGGCTGCCAGGACCTAAATTCCTGGATCAGAGAGTTAGGGCCT
VP1 Parvoduck (1401)  GAGAAATTGGCTTCCAGGACCCAAACTTCTAGACCAAAGGGTAAGAGCAT VP1 Palmivax  (1451)  ACCCAGGAGGAACAGACAATTATGCAAACTGGAACATCTGGAGTAATGGG
VP1 Parvoduck (1451)  ACAGTGGAGGAACAGATAACTATGCGAACTGGTCAATCTGGAGTAAAGGA VP1 Palmivax  (1501)  AACAAGGTGAATTTAAAGGACAGGCAGTATCTCCTACAACCCGGACCTGT
VP1 Parvoduck (1501)  AACAAAGTTTTTCTTAAAGACAGAGAGTATCTCCTGCAACCAGGTCCAGT VP1 Palmivax  (1551)  GTCAGCTACTCACACAGAAAGGGAGGCTTCCAGCATCCCAGCTCAGAATA
VP1 Parvoduck (1551)  AGCTACTACACATACAGAAGATCAGGCTTCCAGTGTACCGGCTCAAAACA VP1 Palmivax  (1601)  TTTTAGGGATAGCTAAAGATCCATACAGATCTGGCAGCACTACAGCAGGA
VP1 Parvoduck (1601)  TAATAGGAATTGCAAAAGACCCCTACAGGTCAGGCAGTACTCTGGCAGGA VP1 Palmivax  (1651)  ATAAGTGATATTATGGTCACGGACGAGCAGGAAGTAGCACCCACAAATGT
VP1 Parvoduck (1651)  ATTTCAGACATCATGGTAACAGATGAGCAAGAAATAGCACCAACTAACGG VP1 Palmivax  (1701)  AGTAGGGTGGAAACCATATGGTAGGACTGTAACGAATGAACAAAACACTA
VP1 Parvoduck (1701)  TGTAGGGTGGAGACCTTATGGATTGACCGTAACCAATGAACAAAACACAA VP1 Palmivax  (1751)  CTACAGCTCCTACAAGTTCAGATCTGGATGTTCTTGGAGCTTTACCAGGA
VP1 Parvoduck (1751)  CAACAGCTCCTACAAACGATGAGCTACAAGTACTGGGAGTACTACCTGGC
```

FIG. 12C

```
VP1 Palmivax   (1801)  ATGGTGTGGCAGAACAGAGATATATATATCTGCAGGGACCTATTTGGGCAAA
VP1 Parvoduck  (1801)  ATGGTCTGGCAGAACAGAGATATTTACCTGCAGGGTCCTATATGGGCTAA VP1 Palmivax   (1851)  AATACCGAAGACTGATGGCAAATTCCATCCTTCTCCAAATCTCGGAGGAT
VP1 Parvoduck  (1851)  AATACCCCAAACAGATGGGAAATTTCATCCTTCTCCAAACCTGGGAGGTT VP1 Palmivax   (1901)  TTGGCCTGCACAATCCACCACCACAGGTCTTCATCAAGAATACACCAGTA
VP1 Parvoduck  (1901)  TTGGTCTCCATAATCCACCTCCCCAGGTCTTTGTTAAAAATACTCCTGTT VP1 Palmivax   (1951)  CCTGCAGACCCTCCAGTAGAATATGTGCACCAGAAGTGGAACTCCTACAT
VP1 Parvoduck  (1951)  CCTGCAGATCCTCCACTAGAGTATGTAAATCAGAAGTGGAATTCTTACAT VP1 Palmivax   (2001)  AACTCAGTACTCTACGGGCCAGTGTACAGTAGAAATGGTGTGGGAGCTGA
VP1 Parvoduck  (2001)  TACACAGTATTCAACAGGGCAGTGTACTGTAGAAATGGTCTGGGAACTCA VP1 Palmivax   (2051)  GAAAAGAGAATTCAAAGAGATGGAACCCAGAAATCCAGTTCACCAGCAAT
VP1 Parvoduck  (2051)  GAAAAGAAAACTCCAAGAGATGGAACCCTGAGATCCAATTTACCAGTAAA VP1 Palmivax   (2101)  TTCAGTAACAGAACAAACATAATGTTTGCACCTAATGAAACTGGTGGATA
VP1 Parvoduck  (2101)  TTTGGAAATAGAACAAGTACTATGTTTGCTCCAAATGAGACTGGAGGCTA VP1 Parvoduck is SEQ ID NO. 1.
VP1 Palmivax is SEQ ID NO. 3.
```

FIG. 13

```
GPV Palmivax VP1    (1)   MSTFLDSFEEWYETAAASWRNLKAGAPQPKPNQQSQSVSPDREPEGKDNN
MDPV Parvoduck VP1  (1)   MSNFLEEFEDWYETAAASWRHLKAGAPKPKSNQQSQSVSTDRKPQRKDNN GPV Palmivax VP1    (51)  RGFVLPGYKYLGPGNGLDKGPPVNKADNVALEHDKAYDLQLKAGDNPYIK
MDPV Parvoduck VP1  (51)  RGFVLPGYKYLGPGNGLDKGPPVNKADNVALEHDKAYDQQLKAGDNPYIK GPV Palmivax VP1    (101) FNHADQDFIDSLQDDHSFGGNLGKAVFQAKKRILEPFGLVEEPINTAPAK
MDPV Parvoduck VP1  (101) FNHADQEFIDNLQGDTSFGGNLGKAVFQAKKRILEPLGLVEEPVNTAPAK GPV Palmivax VP1    (151) KNTGKLTDHYPVVKKPKLTEEVSAGGGSSAVQDGGATAEGTEPVAASEMA
MDPV Parvoduck VP1  (151) KSSGKLTDHYPIVKKPKLSEENSPSRSNSGGEASAAATEGSEPVAAPNMA GPV Palmivax VP1    (201) EGGGGAMGDSSGGADGVGNASGNWHCDSQWMGNTVITKTTRTWVLPSYNN
MDPV Parvoduck VP1  (201) EGGSGAMGDSAGGADGLGNASGNWHCDSQWLGDTVITKTTRTWVLPSYNN GPV Palmivax VP1    (251) HIYKAITSGTSQDANVQYAGYSTPWGYFDFNRFHCHFSPRDWQRLINNHW
MDPV Parvoduck VP1  (251) HIYKAITSGTNPDSNTQYAGYSTPWGYFDFNRFHCHFSPRDWQRLINNHW GPV Palmivax VP1    (301) GIRPKSLKFKIFNVQVKEVTTQDQTKTIANNLTSTIQVFTDDEHQLPYVL
MDPV Parvoduck VP1  (301) GIRPKALKFKIFNVQVKEVTTQDQTKTIANNLTSTIQIFTDNEHQLPYVL GPV Palmivax VP1    (351) GSATEGTMPPFPSDVYALPQYGYCTMHTNQNGARFNDRSAFYCLEYFPSQ
MDPV Parvoduck VP1  (351) GSATEGTMPPFPSDVYALPQYGYCTMHTNQSGARFNDRSAFYCLEYFPSQ GPV Palmivax VP1    (401) MLRTGNNFEFTFDFEEVPFHSMFAHSQDLDRLMNPLVDQYLWNFNEVDSS
MDPV Parvoduck VP1  (401) MLRTGNNFEFSFEFEEVPFHSMFAHSQDLDRLMNPLLDQYLWNFSEVNGG GPV Palmivax VP1    (451) RNAQFKKAVKGAYGTMGRNWLPGPKFLDQRVRAYPGGTDNYANWNIWSNG
MDPV Parvoduck VP1  (451) RNAQFKKAVKGAFGAMGRNWLPGPKLLDQRVRAYSGGTDNYANWSIWSKG GPV Palmivax VP1    (501) NKVNLKDRQYLLQPGPVSATHTEREASSIPAQNILGIAKDPYRSGSTTAG
MDPV Parvoduck VP1  (501) NKVFLKDREYLLQPGPVATTHTEDQASSVPAQNIIGIAKDPYRSGSTLAG GPV Palmivax VP1    (551) ISDIMVTDEQEVAPTNVVGWKFYGRTVTNEQNTTTAPTSSDLDVLGALPG
MDPV Parvoduck VP1  (551) ISDIMVTDEQEIAPTNGVGWRFYGLTVTNEQNTTTAPTNDELQVLGVLPG GPV Palmivax VP1    (601) MVWQNRDIYLQGPIWAKIPKTDGKFHPSPNLGGFGLHNPPPQVFIKNTPV
MDPV Parvoduck VP1  (601) MVWQNRDIYLQGPIWAKIPQTDGKFHPSPNLGGFGLHNPPPQVFVKNTPV GPV Palmivax VP1    (651) PADPPVEYVHQKWNSYITQYSTGQCTVEMVWELRKENSKRWNPEIQFTSN
MDPV Parvoduck VP1  (651) PADPPLEYVNQKWNSYITQYSTGQCTVEMVWELRKENSKRWNPEIQFTSK GPV Palmivax VP1    (701) FSNRTNIMFAPNETGGYVEDRLIGTRYLTQNL
MDPV Parvoduck VP1  (701) FGNRTSTMFAPNETGGYVEDRLIGTRYLTQNL MDPV Parvoduck VP1 is SEQ ID NO. 2.
GPV Palmivax VP1 is SEQ ID NO. 4.
```

ATTENUATED PARVOVIRUS VACCINE FOR MUSCOVY DUCK PARVOVIRUS AND GOOSE PARVOVIRUS (DERZSY'S DISEASE)

CROSS-REFERENCE TO RELATED APPLICATION

This application is a divisional application of U.S. application Ser. No. 14/427,197 filed on Mar. 10, 2015, which claims the benefit of U.S. Provisional Application No. 61/698,842, filed Sep. 10, 2012.

FIELD OF THE INVENTION

The present invention relates generally to attenuated viral vaccines, particularly those providing broad, safe, and effective protection to palmipeds against infections or diseases. The invention further relates to methods of producing the attenuated virus, and to the identification of variations in the nucleotide sequence that are associated with decreased virulence of the attenuated virus.

BACKGROUND OF THE INVENTION

Goose parvovirus (GPV; also called Derzsy's Disease) and Muscovy duck parvovirus (MDPV) are antigenically distinct viruses that affect palmipeds. GPV is highly contagious and is characterized by multiple clinical signs, including anorexia, prostration, weakness and polydipsia. GPV may present in acute, subacute or chronic forms; the acute form of the disease may cause 100% mortality in goslings under 10 days of age. GPV primarily affects geese and Muscovy ducks (*Cairina moschata*). Currently, goose and Muscovy duck producers may protect against GPV using an attenuated live vaccine.

MDPV is an acute systemic infection of Muscovy ducklings. The clinical signs of MDPV are similar to those of GPV and the mortality rate can be 80% or higher. MDPV is transmitted horizontally and can also be transmitted vertically when susceptible hens become infected during lay or if there is reactivation of latency. To date, MDPV is known to affect only Muscovy ducks while other avian species are not susceptible. No attenuated live vaccine currently exists for combatting MDPV although an inactivated vaccine is available.

Accordingly, Muscovy ducks are vulnerable to both GPV and MDPV. Given the similarity with which both diseases present, it is difficult to determine which vaccine to administer, as the vaccine for GPV is ineffective against MDPV and the MDPV vaccine is ineffective against GPV. Muscovy duck producers may then administer vaccines against both diseases or face the economic hardship associated with the above-mentioned mortality rates.

Administering two vaccinations is less than ideal for logistical and economic reasons.

SUMMARY OF THE INVENTION

In one embodiment, the invention is a composition comprising an attenuated palmiped parvovirus capable of providing a heterologous immune response in palmipeds against Muscovy duck parvovirus and goose parvovirus (Derzsy's Disease). In one aspect, the composition of the attenuated palmiped parvovirus comprises a polynucleotide encoding viral protein 1 (VP1) having the sequence as set forth in SEQ ID NO. 2. See FIG. 13. In another aspect, the composition of the attenuated palmiped parvovirus comprises a polynucleotide having the sequence as set forth in SEQ ID NO. 1. See FIG. 12.

In another embodiment, the invention is an attenuated palmiped parvovirus capable of providing a heterologous immune response in palmipeds against Muscovy duck parvovirus and goose parvovirus (Derzsy's Disease). In one aspect, the attenuated palmiped parvovirus comprises a polynucleotide encoding viral protein 1 (VP1) having the sequence as set forth in SEQ ID NO. 2. In another aspect, the attenuated palmiped parvovirus comprises a polynucleotide having the sequence as set forth in SEQ ID NO. 1.

In yet another embodiment, the invention is a method of treating a palmiped against Muscovy duck parvovirus and goose parvovirus (Derzsy's Disease) comprising the step of administering a composition comprising an attenuated palmiped parvovirus capable of providing a heterologous immune response in palmipeds against Muscovy duck parvovirus and goose parvovirus (Derzsy's Disease). In one aspect, the composition comprises the attenuated palmiped parvovirus comprising a polynucleotide encoding viral protein 1 (VP1) having the sequence as set forth in SEQ ID NO. 2. In another aspect, the composition comprises the attenuated palmiped parvovirus comprising a polynucleotide having the sequence as set forth in SEQ ID NO. 1.

In yet another embodiment, the invention is an isolated polynucleotide encoding the polypeptide having the sequence as set forth in SEQ ID NO. 2. The invention is further an isolated polynucleotide having the sequence as set forth in SEQ ID NO. 1.

As defined herein, the term "gene" will be used in a broad sense, and shall encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure. When a specific sequence is discussed, for example, the sequence as set forth in SEQ ID NO. # (the DNA sequence equivalent of parental virus cRNA "sense" strand), the skilled person will instantly be in possession of all derivable forms of that sequence (mRNA, vRNA, cRNA, DNA, protein, etc.). A skilled person using the genetic code can routinely derive from a DNA sequence the vRNA, cRNA, and peptide sequences.

In a particular embodiment, the attenuated vaccine comprises an adjuvant. The adjuvant may be any substance which increases and/or augments the elicited immune response, as compared to attenuated vaccine alone. Mucosal adjuvants, including chitosans and derivatives thereof, are particularly useful for the disclosed oral attenuated vaccines.

The invention further provides methods for inducing an immunological (or immunogenic) or protective response against GPV and MDPV, as well as methods for preventing or treating GPV and MDPV, or disease state(s) caused by the same, comprising administering the attenuated virus, or a composition comprising the attenuated virus to animals in need thereof.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 4*a* shows mean weight data for ducklings aged 1 day at D0 tested with strain GM72.

FIG. 4*b* shows mean weight data for ducklings aged 8 days at D0 tested with strain GM72.

FIG. 5 shows body weight data for ducklings tested with strain GM87.

FIGS. 12A-12C show a partial nucleotide sequence comparison of the VP1 (viral protein 1) gene between the Palmivax vaccine for GPV (SEQ ID NO. 3) and the invention (i.e., Parvoduk; SEQ ID NO. 1).

FIG. 13 shows the protein sequence comparison of the VP1 gene between the Palmivax vaccine for GPV (SEQ ID NO. 4) and the invention (i.e., Parvoduck protein sequence; SEQ ID NO. 2).

DETAILED DESCRIPTION OF THE INVENTION

Figure 1:
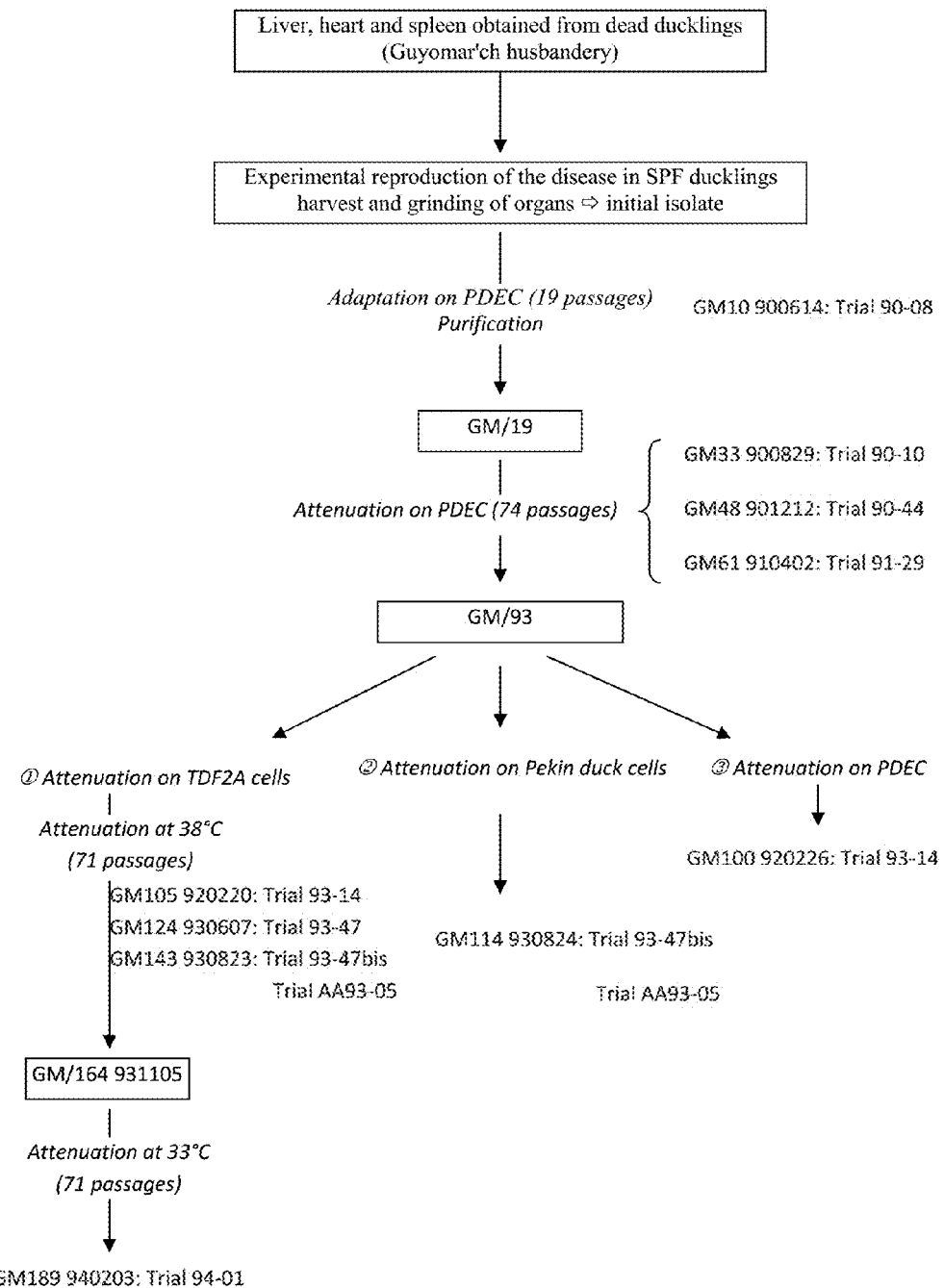
FIG. 1 is a history of passages and corresponding safety studies.

The present invention provides nucleotide sequences and genes involved in the attenuation of a microorganism, such as virus, for instance, parvovirus, products (e.g., proteins, antigens, immunogens, epitopes) encoded by the nucleotide sequences, methods for producing such nucleotide sequences, products, micro-organisms, and uses therefor, such as for preparing vaccine or immunogenic compositions or for eliciting an immunological or immune response or as a vector, e.g., as an expression vector (for instance, an in vitro or in vivo expression vector).

Mutations introduced into nucleotide sequences and genes of micro-organisms produce novel and nonobvious attenuated mutants. These mutants are useful for the production of live attenuated immunogenic compositions or live attenuated vaccines having a high degree of immunogenicity.

Identification of the mutations provides novel and nonobvious nucleotide sequences and genes, as well as novel and nonobvious gene products encoded by the nucleotide sequences and genes.

In an embodiment, the invention provides an attenuated palmiped parvovirus capable of providing a heterologous immune response in palmipeds against Muscovy duck parvovirus and goose parvovirus.

In another aspect, the invention provides immunological composition comprising an attenuated MDPV strain that provides a heterologous immune response in palmipeds against Muscovy duck parvovirus and goose parvovirus. In one embodiment, the compositions may further comprise a pharmaceutically or veterinary acceptable vehicle, diluent or excipient.

In an embodiment, the invention provides methods of vaccinating an animal comprising at least one administration of the compositions comprising sequences encoding an attenuated MDPV strain that provides a heterologous immune response in palmipeds against Muscovy duck parvovirus and goose parvovirus.

The invention further encompasses gene products, which provide antigens, immunogens and epitopes, and are useful as isolated gene products.

Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides a virus containing attenuating mutations in a nucleotide sequence or a gene wherein the mutation modifies the biological activity of a polypeptide or protein encoded by a gene, resulting in attenuated virulence of the virus.

In particular, the present invention encompasses attenuated parvovirus strains and vaccines comprising the same, which elicit an immunogenic response in an animal, particularly a attenuated parvovirus strain that elicits, induces or stimulates a response in a Muscovy duck.

The particular MDPV attenuated strain of interest has mutations relative to the virulent parent strain.

In another aspect, the novel attenuated parvovirus strain is formulated into a safe, effective vaccine against GPV and MDPV.

In an embodiment, the attenuated parvovirus vaccine further comprises an adjuvant. In a particular embodiment, the adjuvant is a mucosal adjuvant, such as chitosan, methylated chitosan, trimethylated chitosan, or derivatives or combinations thereof. Other adjuvants are well known to those of skill in the art.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended palmipeds; specifically Muscovy ducks.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

"Heterologous" with respect to the claimed invention means a composition that confers protective immunity against a pathogen that shares cross-reacting antigens with the microorganisms in the vaccine. For example, a vaccine made from the composition of the claimed invention confers immunity to palmipeds against Muscovy Duck Parvovirus (MDPV) and Goose Parvovirus (GPV or Derzsy Disease).

Methods of Use and Article of Manufacture

The present invention includes the following method embodiments. In an embodiment, a method of vaccinating an animal comprising administering a composition comprising an attenuated palmiped parvovirus capable of providing a heterologous immune response in waterfowl against Muscovy duck parvovirus and goose parvovirus (Derzsy's Disease) and a pharmaceutical or veterinarily acceptable carrier, excipient, or vehicle to an animal is disclosed.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations. By way of example, the "prime" could comprise the modified live virus of the invention alone while the "boost" could comprise the modified live virus of the invention with an adjuvant.

The dose volume of compositions for target species is generally between about 0.1 to about 2.0 ml, between about 0.1 to about 1.0 ml, and between about 0.5 ml to about 1.0 ml.

The efficacy of the vaccines may be tested after the last immunization by challenging animals with a virulent strain of GPV or MDPV. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of parvovirus-specific antibody.

The compositions comprising the attenuated viral strains of the invention used in the prime-boost protocols are contained in a pharmaceutically or veterinary acceptable vehicle, diluent or excipient. The protocols of the invention protect the animal from parvovirus and/or prevent disease progression in an infected animal.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against parvovirus in an animal comprising an attenuated MDPV immunological composition or vaccine and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

Choice of Vaccine Strain

The viral strain was isolated from liver of ducks originating from SPF (specific pathogen-free) flocks. These ducks were introduced onto a farm of the Guyomarc'h company struck down by the "MMFC" syndrome (Mortality, Malnutrition, Featherlessing, Crawling syndrome). The isolated virus obtained was named GM and it was inoculated to 7 SPF ducklings aged one day. These ducklings died 5 to 9 days after inoculation. The livers, hearts and spleens of these ducklings were removed and ground. The ground product was propagated successively 20 times in SPF duck embryo primary cells, with 3 cloning in limit dilutions, at the seventeenth, the eighteenth and the nineteenth passages. Then, the harvest of the twentieth passage underwent 179 passages in duck embryo cells before establishing the Master Seed Virus. The GM strain has thus been attenuated by a large number of passages in duck embryo cells before being used for the production of the final vaccine product (i.e., Parvoduck vaccine). Its characteristics are those of the parvovirus but without the pathogenic properties of wild strains.

In addition, the wild parvovirus in ducks being deemed stable, this strain is perfectly suited to the production of a vaccine against both the MDPV and GPV.

Methodology

The GM strain was adapted for growth on primary duck embryo cells (PDEC) as mentioned above and then purified. Another 74 attenuation passages were then carried out on PDEC (until strain GM93, ie 93 passages after the initial isolate). From this level, the strain was attenuated on either TDF2A cell line, PDEC or Pekin duck cells. The safety of the passaged strains was tested in SPF ducklings by successive studies in order to determine the most appropriate attenuation level for use as live modified vaccine. The passages are diagrammed in FIG. 1.

EXAMPLES

Example 1—LD50 of GPV Viral Strain GM10 in Ten-Day-Old SPF Ducklings

Strain: GM10, titrating 7.5 log 10 CCID50/ml.

Animals: 24 SPF ten-day-old ducklings, divided into 4 groups of 6 and inoculated at D0 as in Table 1:

TABLE 1

| Group | Strain | Dose * | Volume (ml) | Route |
|---|---|---|---|---|
| G1 | GM10 | 7.2 (non diluted) | 0.5 | IM |
| G2 | GM10 | 5.2 | 0.5 | IM |
| G3 | GM10 | 3.2 | 0.5 | IM |
| G4 | GM10 | 1.2 | 0.5 | IM |

* log10 CCID50 per bird

Monitoring: Clinical follow-up, D0 to D21. Scoring: (0) healthy (1) locomotor problems (2) lameness (3) paresis (4) death.

Figure 2:
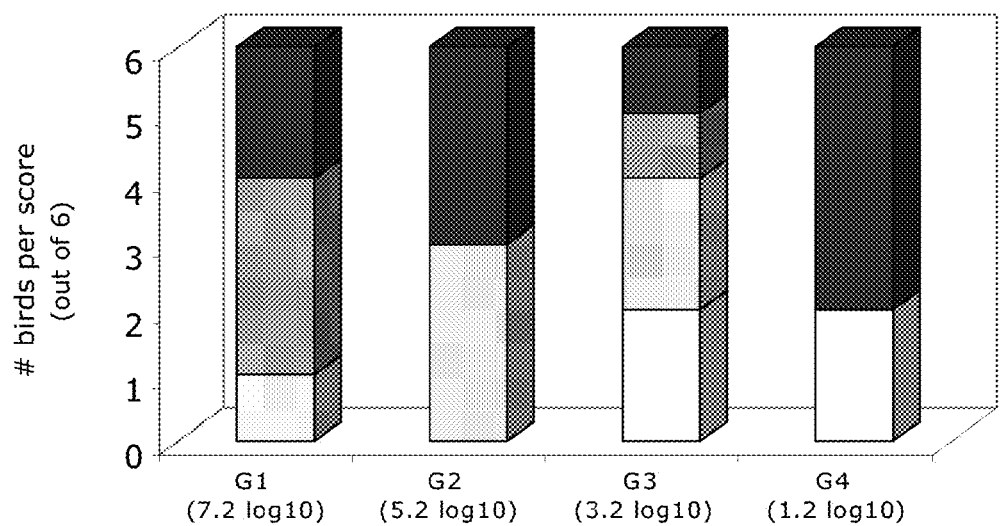
FIG. 2 shows clinical data for strain GM10.

Clinical signs observed appeared as from D8 in all the groups. FIG. 2 shows the number of birds per clinical scores (highest score reached by the birds throughout the observation period). No birds remained unaffected by the disease all through the study. At D21, one bird in G1, 2 in G3 and 2 in G4 had recovered from the disease and were found as healthy.

The conclusion is that GM10 passage was not sufficiently attenuated since it induced severe locomotor symptoms in a large majority of birds, whatever the dose used. Considering the results obtained, the LD50 was not calculated.

Example 2—Pathogenicity of Strain GM33 in One-Day-Old SPF Ducklings

Strain: GM33 titrating 8.2 log 10 CCID50/ml.
Animals: 10 SPF one-day-old ducklings, subcutaneously inoculated on D0 with 6.0 log 10 CCID50 of strain GM33 under a volume of 0.5 ml.
Monitoring: Mortality follow-up, D0 to D21. Birds which died during the study were necropsied.
Necropsy at D21 for lesions of Derzsy's disease (spleen and/or liver enlargement, ascites, hydropericarditis). Blood sampling at D21 and search for specific duck parvovirus antibodies by SN (i.e., sereoneutralization assay to measure virus neutralizing antibody titers). Data shown in Table 2.

TABLE 2

Clinical and post-mortem (pm) results

| | | | Observations at D 21 | | |
|---|---|---|---|---|---|
| Mortality, D 0 to D 21 | | | # sick | | #birds |
| # birds | # with pm lesions [a] | # surviving birds | bird [b]s | # birds with growth lag [c] | with pm lesions [a] |
| 4/10 | 4/4 | 6/10 | 0/6 | 6/6 | 2/6 |

[a] post-mortem lesions: spleen and/or liver enlargement, ascites, hydropericarditis
[b] ie bad general condition, anorexia, lameness
[c] clinical assessment (no weighing)

All the sera showed high GM antibody titres, ranging from 3.4 to 4.0 log 10 SN unit (positive reference serum: 2.8 log 10 SN unit). These results validated the inoculation. Inoculation of 6.0 log 10 CCID50 of GM33 strain induced 40% mortality and 100% morbidity (considering the growth retardation in all the birds) in one-day-old SPF ducklings.

Example 3—Pathogenicity of Strain GM48 in One-Day-Old SPF Ducklings

Strain: GM48, titrating 8.0 log 10 CCID50/ml.
Animals: 10 SPF one-day-old ducklings, subcutaneously inoculated on D0 with 6.0 log 10 CCID50 of strain GM48 under a volume of 0.5 ml.
Monitoring: Mortality follow-up, D0 to D21. Birds which died during the study were necropsied. See Table 3. Necropsy at D21 for lesions of Derzsy's disease (spleen enlargement, hepatitis, ascites, hydropericarditis, aerosacculitis).

TABLE 3

Clinical and post-mortem (pm) results

| Mortality, D0 to D21 | | Observations at D21 | | | |
|---|---|---|---|---|---|
| # birds | # with pm lesions [a] | # surviving birds | # sick bird [b]s | # birds with growth lag [c] | # birds with pm lesions [a] |
| 1/10 | 1/1 | 9/10 | 0/9* | 3/9* | 5/9** |

[a] post-mortem lesions: spleen and/or liver enlargement, ascites, hydropericarditis
[b] ie bad general condition, anorexia, lameness
[c] clinical assessment (no weighing)
*the 3 birds with growth retardation had showed severe lameness at D7, but had recovered from the disease at the final examination
**all 3 birds with growth retardation showed pm lesions.

Inoculation of 6.0 log 10 CCID50 of GM48 strain induced 10% mortality and 60% morbidity (considering growth retardation+post-mortem observations at D21) in one-day-old SPF ducklings.

Example 4—Pathogenicity of Strain GM61 in One-Day-Old SPF Ducklings

Strain: GM61, titrating 8.6 log 10 CCID50/ml.
Animals: 16 SPF one-day-old ducklings, divided into 2 groups and inocualted at D0 as in Table 4.

TABLE 4

| Group | n | Strain | Dose* | Volume (ml) | Route |
|---|---|---|---|---|---|
| G1 | 11 | GM61 | 6.0 | 0.5 | SC |
| G2 | 5 | Non-inoculated contact birds | | | |

*log10 CCID50 per bird

Monitoring: Mortality follow-up, D0 to D21. Birds which died during the study were necropsied.
Weighing and sexing at D21. Necropsy at D21 for lesions of Derzsy's disease. Histological examination of brain, heart, spleen, liver, tendon and leg muscle (G1: pooled samples; G2 individual samples). Blood sampling at D21 and search for specific duck parvovirus antibodies by SN. The results are summarized in Table 5. Positive reference serum: 2.8 log 10 SN unit.

TABLE 5

| | | SN Titres | |
|---|---|---|---|
| Group | Treatment | Mean SN value (log10) | Range of values |
| G1 | 6.0 log10 CCID50 - GM61 | >3.7 | 2.8->4.0 log10 |
| G2 | Non-inoculated contacts | 2.8 | 2.2-3.4 |

These results validated the inoculation and confirmed the spread of the virus to contact birds G2.

There was one non-specific death in G1 on D1. No other bird was found dead nor sick all through the trial. Further, no G1 bird showed any lesion at necropsy at D21. In G2, 2 ducks showed ascites and perihepatitis, suggesting that the virus spread to contact birds G2.

Figure 3:
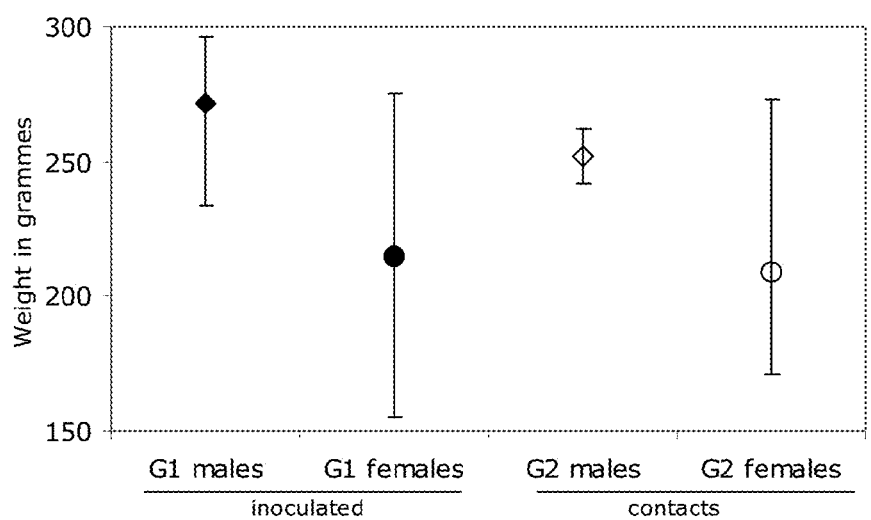
FIG. 3 shows mean weight data for ducklings tested with strain GM61.

FIG. 3 shows the mean weights observed per group and per sex, as well as weight ranges within each of these subgroups. The results observed were comparable in G1 and G2. Inflammatory lesions of moderate intensity were observed in the majority of the samples. Slight encephalitis and myositis lesions were seen, as classically observed in parvovirus infection.

Rather surprisingly, tenosynovitis was also observed in almost all the samples.

Inoculation of 6.0 log 10 CCID50 of GM61 strain to one-day-old SPF ducklings induced no mortality and very low morbidity from the clinical standpoint. Histopathology suggested that the safety of the strain was not complete. The data obtained also indicated that GM61 had a high ability to spread between birds.

Example 5—Safety of Strain GM72 in SPF Ducklings

Strain: GM72, titrating 6.0 log 10 CCID50/ml (freeze-dried).

Animals: 26 SPF one-day-old ducklings, and 20 SPF 8-day-old ducks inoculated at D0 as shown in Table 6.

TABLE 6

| Group | Age (days) | n | Strain | Dose* | Volume (ml) | Route |
|---|---|---|---|---|---|---|
| G1 | 1 | 16 | GM72 | 5.0 | 0.5 | SC |
| G2 | 1 | 10 | Non-inoculated controls | | | |
| G3 | 8 | 10 | GM72 | 5.0 | 0.5 | SC |
| G4 | 8 | 10 | Non-inoculated controls | | | |

*log10 CCID50 per bird

Monitoring: Mortality follow-up, D0 to D21, weighing at D0 and D21, sexing and necropsy for lesions of Derzsy's disease at D21. Histological examination of brain, heart, spleen, liver, tendon and leg muscle of 4 birds per group. Blood sampling at D21 and search for specific duck parvovirus antibodies by SN. Observation: The one-day-old ducklings were in bad general condition at delivery.

Within each age category, the same pattern was observed: homogeneous bodyweights at D0, discrepancy between the vaccinates and the controls 3 weeks post-inoculation, with a clear growth lag in the inoculated birds. As expected, the sexual dimorphism was more marked in the older birds (G3/G4).

Clinical and post-mortem findings: There were 3 non-specific deaths in G1 (GM72-inoculated at one-day-old) on D1. Two ducks also died in G3 (GM72-inoculated at 8-day-old) at D6 and D15 respectively. No other bird was found dead nor sick all through the trial. Necropsy results at D21 are summarized in Table 7.

Post-mortem observations in G2 and G4 controls suggested that there was a virus spread during the study. All the samples examined showed very discreet inflammatory lesions, generally consisting of congestion sometimes associated with small lymphoid infiltrates. The lesions observed were all of slight intensity and showed no specificity; no differences were seen between the 4 groups.

Serology results at D21 are summarized in Table 8. Positive reference serum: 2.8 log 10 SN unit.

TABLE 8

| | | SN Titres | |
|---|---|---|---|
| Group | Treatment | Mean SN value (log10) | Range of values |
| G1 | 5.0 log10 CCID50 of GM72 at one-day-old | 3.12 | 2.8-4.0 log10 |
| G2 | Non-inoculated controls for G1 (1-day-old) | ≤0.4 | All ≤0.4 |
| G3 | 5.0 log10 CCID50 of GM72 at 8-day-old | 3.3 | 2.8-4.0 log10 |
| G4 | Non-inoculated controls for G3 (8-day-old) | 3.3 | 2.8-4.0 log10 |

Serology titres in the inoculated groups G1 and G3 confirmed the virus take. The antibody level in G4 controls confirmed the previous assumption of a virus spread based on the post-mortem results. On the contrary, there was no serological changes in G2 controls; the spleen lesions observed at necropsy in this group was probably due to a late virus spread with no seroconversion before the end of the study. In both cases, the virus spread had no major influence on the bodyweight gain in the controls.

Zootechnical problems (non-specific mortality due to bad general condition of the birds at delivery and viral spread) interfered with a reliable interpretation of the study. The results available suggested yet that even if there was no impact of GM72 strain from the histology standpoint, inoculation of the strain at either 1 or 8 days of age induced patent growth lag.

Example 6—Safety of Strain GM87 in One-Day-Old SPF Ducklings

Strain: GM87.

Animals: 30 SPF one-day-old ducklings, divided into 2 groups and inocualted at D0 as shown in Table 9.

TABLE 7

| | | | Number of lesions observed, per type[b] | | | Birds |
|---|---|---|---|---|---|---|
| Group | Treatment | n[a] | Ascitis | Myocarditis | Hepatitis | Marbled spleen | with no lesions |
| G1 | 5.0 log10 CCID50 of GM72 at one-day-old | 13 | 3 | 1 | 1 | 4 | 6/13 |
| G2 | Non-inoculated controls for G1 | 10 | 0 | 0 | 0 | 8 | 2/10 |
| G3 | 5.0 log10 CCID50 of GM72 at 8-day-old | 8 | 0 | 0 | 0 | 0 | 8/8 |
| G4 | Non-inoculated controls for G3 | 10 | 1 | 0 | 0 | 1 | 8/10 |

[a]number of birds examined at D21
[b]Some birds can show different types of lesions

TABLE 9

| Group | n | Strain | Dose* | Volume (ml) | Route |
|---|---|---|---|---|---|
| G1 | 15 | GM87 | 6.2 | 0.5 | Sc |
| G2 | 15 | | Non-inoculated controls | | |

*log10 CCID50 per bird - actual dose given, ie inoculum titrated at D0.

Monitoring: Mortality follow-up, D0 to D21 (not necropsied), weighing at D0 and D21. Euthanasia at D21, sexing and necropsy for lesions of Derzsy's disease. Histological examination of brain, heart, spleen, liver, tendon and leg muscle of 4 birds per group (individual samples).

Blood sampling at D21 and search for specific duck parvovirus antibodies by SN.

Serology results are summarized in Table 10. Positive reference serum: 3.4 log 10 SN unit.

TABLE 10

| | | SN Titres | |
|---|---|---|---|
| Group | Treatment | Mean SN value (log10) | Range of values |
| G1 | 6.0 log10 CCID50 - GM87 | >3.2 | 2.2->4.0 log10 |
| G2 | Non-inoculated controls | 2.8 | 2.2-3.4 |

These results validated the inoculation in G1. The relatively high antibody titres in G2 suggested that a viral spread occurred during the study.

Clinical and post-mortem findings: there was a non-specific death in the controls at D2.

In the GM87-inoculated group G1, there were 6 deaths between D4 and D18. Necropsy results at D21 are summarized in Table 11.

TABLE 11

| | | | Number of lesions observed, per type[b] | | | Birds |
|---|---|---|---|---|---|---|
| Group | Treatment | n[a] | Ascitis | Aerosacculitis | Heart lesions[c] | Liver lesions[d] | with no lesions |
| G1 | 6.0 log10 CCID50 - GM87 | 9 | 2 | 3 | 4 | 6 | 0/9 |
| G2 | Non-inoculated controls | 13 | 4 | 3 | 4 | 4 | 9/13 |

[a] number of birds examined at D21 - NB:in G2, one bird was omitted at necropsy by mistake
[b] Most birds showed at least 2 different types of lesions
[c] Fibrinous pericarditis and/or myocarditis
[d] Fibrinous perihepatitis and/or necrosed hepatitis FIG. 5 shows the shows the bodyweight changes observed per group and per sex, from D0 to D21. G1 are vaccinates; G2 are controls. The results observed were comparable in G1 and G2. As compared to other studies conducted in ducks, the bodyweights at D21 were very low in both groups (approximately one third of the weight expected).

The main lesions observed were at the hepatic level. Some of them, such as perihepatitis and necrosis, were rather evocative of a bacterial infection. Lesions of myocarditis, myositis and encephalitis—classically observed in parvovirus infection—were rare and of slight intensity. There were no differences in the histopathological observations in the 2 groups regarding frequency or intensity of the lesions. Zootechnical problems (viral spread and intercurrent bacterial infection) did not allow to interpret the safety data on a reliable basis. The higher mortality recorded in the inoculated birds and the bad growth data suggested that the GM87 strain was still not attenuated enough.

Example 7—Safety of Strain GM100/PDEC and GM105/TDF in One-Day-Old SPF Ducklings Strains: GM100 grown on PDEC (herein named GM100/PDEC)—8.7 log 10 CCID50/ml;
GM105 grown on TDF2A cells (herein named GM105/TDF)—8.2 log 10 CCID50/ml.
Animals: 30 SPF one-day-old not-sexed ducklings inoculated at D0 as shown in Table 12.

TABLE 12

| Group | n | Strain | Dose* | Volume (ml) | Route |
|---|---|---|---|---|---|
| G1 | 10 | GM100/PDEC | 5.0 | 0.2 | SC |
| G2 | 10 | GM105/TDF | 5.0 | 0.2 | SC |
| G3 | 10 | | Non-inoculated controls | | |

*log10 CCID50 per bird

Monitoring: Mortality follow-up, D0 to D21. Weighing at D0, D10 and D21.

Figure 6:
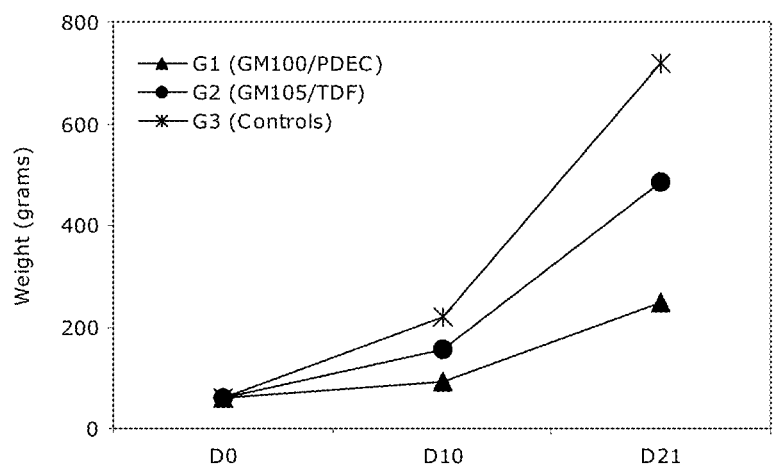
FIG. 6 shows body weight data for ducklings tested with strain GM100/PDEC and for ducklings tested with strain GM105/TDF.

There were 2 non-specific deaths during the study: one in G1 (GM100/PDEC) at D3 and one in G3 (controls) at D2. In G1, 2 other deaths were recorded at D10 and D18, and considered as related to the strain inoculation. Weighing results are shown in FIG. 6. Ducks are aged 1 day at D0.

Inoculation of 5.0 log 10 CCID50 of GM100/PDEC strain induced 30% mortality and 100% morbidity (considering growth retardation at D21) in one-day-old SPF ducklings.

Inoculation of 5.0 log 10 CCID50 of GM105/TDF strain to one-day-old SPF ducklings induced no mortality. The safety of the strain was yet not complete, since it induced a significant growth lag—even if less marked than for strain GM100/PDEC—as compared to the controls.

Example 8—Safety of Strain GM124 in One-Day-Old SPF Ducklings

Strain: GM124 grown on TDF2A cells (herein named GM124/TDF)—8.7 log 10 CCID50/ml.
Animals: 24 SPF one-day-old ducklings inoculated at D0 as shown in Table 13.

TABLE 13

| Group | N | Strain | Dose* | Volume (ml) | Route |
|---|---|---|---|---|---|
| G1 | 12 | GM124/TDF | 5.0 | 0.2 | SC |
| G2 | 12 | | Non-inoculated controls | | |

*log10 CCID50 per bird

Monitoring: Mortality follow-up, D0 to D21. Weighing at D0 (group randomisation), D10 and D21. Necropsy at D21 for lesions of Derzsy's disease and sexing.

Figure 7:
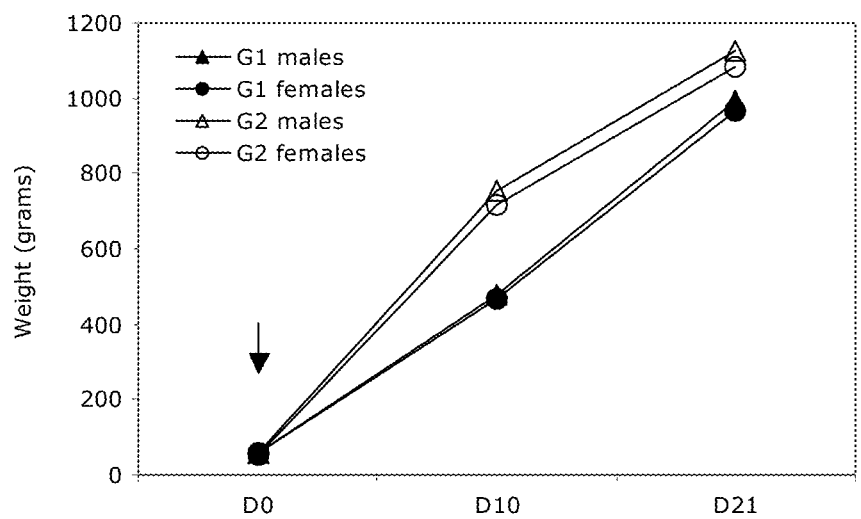
FIG. 7 shows body weight data for ducklings tested with strain GM124.

Mortality follow-up and post-mortem lesions: there was only one non-specific death in G1 (GM124/TDF) at D3. No other death was recorded during the study. No specific lesions attributable to the virus strain was observed at necropsy. Weighing results are shown in FIG. 7. There was a difference in the bodyweights in the 2 groups, particularly at D10. It should yet be highlighted that the sex ratio was different in the 2 groups (73% females in G1 vs. 17% in G2) which might have played a role in this observation. Ducks are aged 1 day at D0. G1 are vaccinates and G2 are controls.

Even if strain GM124/TDF seems safe on a clinical and necropsy basis, the data suggest that it still has an adverse affect on bird growth.

Example 9—Safety of Strain GM114/Pekin and GM143/TDF in One-Day-Old SPF Ducklings Strains: GM143 grown on TDF2A cells (herein named GM143/TDF)—8.2 log 10 CCID50/ml.

GM114 grown on Pekin cells (herein named GM114/Pekin)—6.3 log 10 CCID50/ml.

Animals: 30 SPF one-day-old ducklings inoculated at D0 as shown in Table 14.

TABLE 14

| Group | n | Strain | Dose* | Volume (ml) | Route |
|---|---|---|---|---|---|
| G1 | 10 | GM143/TDF | 5.0 | 0.2 | SC |
| G2 | 10 | GM114/Pekin | 5.0 | 0.2 | SC |
| G3 | 10 | Non-inoculated controls | | | |

*log10 CCID50 per bird

Monitoring: Mortality follow-up, D0 to D21. Weighing at D0 (group randomisation), D10 and D21. Necropsy at D21 for lesions of Derzsy's disease and sexing. Blood sampling at D21 and search for specific duck parvovirus antibodies by SN.

Mortality follow-up and post-mortem observations: There was one non-specific death in G1 (GM143/TDF) at D1. No other death occurred during the study. All the inoculated ducks from G1 and G2 showed lesions at necropsy at the beak and/or heart and/or liver and/or spleen level. There were no lesions observed in the controls (G3).

Figure 8:
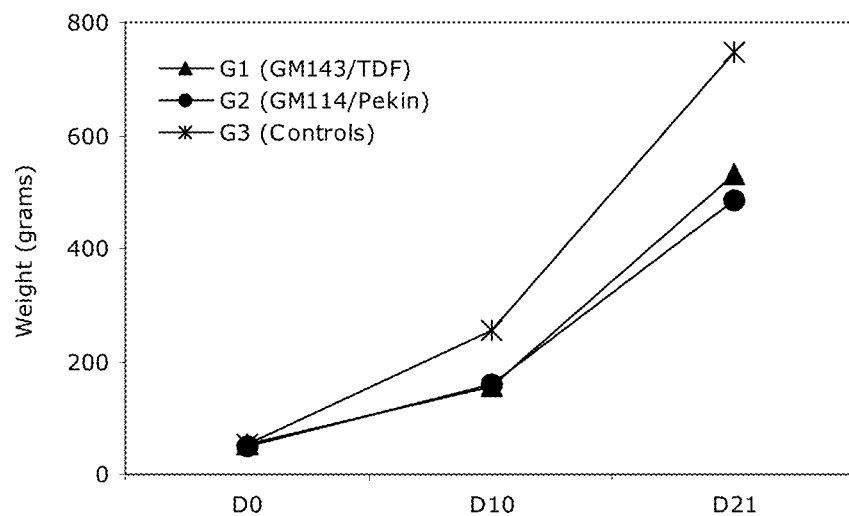
FIG. 8 shows body weight data for ducklings tested with strain GM114/Pekin and for ducklings tested with strain GM143/TDF.

Weighing results are shown in FIG. 8. Serology results at D21 are summarized in Table 15.

Positive reference serum: 2.8 log 10 SN unit.

TABLE 15

| | | SN Titres | |
|---|---|---|---|
| Group | Treatment | Mean SN value (log10) | Range of values |
| G1 | 5.0 log10 CCID50 - GM143/TDF | 2.3 | 1.6-2.8 log10 |

TABLE 15-continued

| | | SN Titres | |
|---|---|---|---|
| Group | Treatment | Mean SN value (log10) | Range of values |
| G2 | 5.0 log10CCID50 - GM114/Pekin | 2.5 | 2.2-3.4 log10 |
| G3 | Non-inoculated controls | ≤0.4 | All sera ≤0.4 |

These results validated the inoculation.

Inoculation of 5.0 log 10 CCID50 of GM143/TDF strain and of GM114/Pekin to one-day-old SPF ducklings induced no mortality. Both strains resulted in high morbidity, considering the numerous post-mortem lesions observed and the growth retardation in inoculated birds as compared with control ducks.

Example 10—Safety of Strain GM114/Pekin and GM143/TDF in 15-Day-Old SPF Ducklings Strains: GM143 grown on TDF2A cells (herein named GM143/TDF)—8.2 log 10 CCID50/ml.

GM114 grown on Pekin cells (herein named GM114/Pekin)—6.3 log 10 CCID50/ml.

PALMIVAX, batch 3PMX4B122 (herein named PMX)—5.6 log 10 CCID50 per vial.

Diluent: diluent for live duck vaccines, batch 3SPP250311.

Animals: 40 SPF 15-day-old ducklings inoculated at D0 as shown in Table 16.

TABLE 16

| Group | n | Strain | Dose * | Volume (ml) | Route |
|---|---|---|---|---|---|
| G1 | 10 | GM143/TDF | 5.0 | 0.2 | SC |
| G2 | 10 | GM114/Pekin | 5.0 | 0.2 | SC |
| G4 | 10 | PMX | 5.0 | 0.2 | SC |
| G4 | 10 | Controls, injected with diluent only | | | |

*log10 CCID50 per bird

Monitoring: Mortality follow-up, D0 to D21. Weighing at D0 (group randomisation), D9 and D21. Sexing at D21.

There was no death in any groups all through the study.

Figure 9:
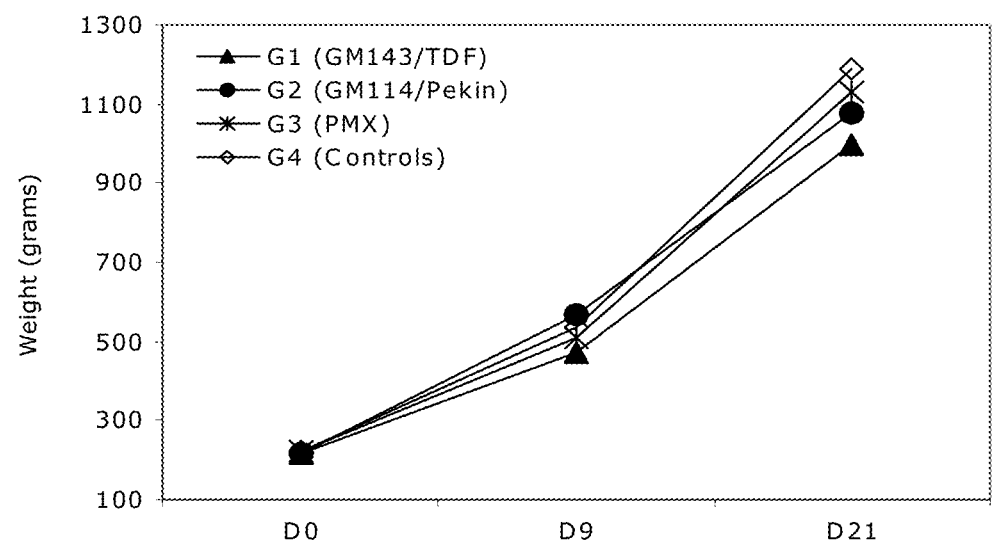
FIG. 9 shows body weight data for ducklings tested with strain GM114/Pekin, strain GM143/TDF and with the Palmivax (PMX) vaccine.

FIG. 9 shows the mean bodyweights measured per group at each weighing date (the sex ratio being very close in the 4 groups, the sex influence was considered as negligible). Ducks were aged 15 days at D0.

Inoculation of 5.0 log 10 CCID50 of GM143/TDF strain and of GM114/Pekin to 15-day-old SPF ducklings induced no mortality. Both strains yet resulted in growth retardation as compared with non-inoculated controls ducks and PALMIVAX vaccinates.

Example 11—Safety of Strain GM131/Pekin and GM189/TDF in SPF Ducklings

Strains: GM189 grown on TDF2A cells (herein named GM189/TDF)—7.8 log 10 CCID50/ml;

GM131 grown on Pekin cells (herein named GM131/Pekin)—6.2 log 10 CCID50/ml.

Diluent: Diluent for live duck vaccines, batch 3SPP250311.

Animals: 33 SPF one-day-old ducklings, and 29 SPF 15-day-old ducks inoculated at D0 as shown in Table 17.

TABLE 17

| Group | Age (days) | n | Strain | Dose * | Volume (ml) | Route |
|---|---|---|---|---|---|---|
| G1 | 1 | 11 | GM189/TDF | 5.0 | 0.2 | SC |
| G2 | 1 | 11 | GM131/Pekin | 5.0 | 0.2 | SC |
| G3 | 1 | 11 | Controls, injected SC with diluent | | | |
| G4 | 15 | 10 | GM189/TDF | 5.0 | 0.2 | SC |
| G5 | 15 | 10 | GM131/Pekin | 5.0 | 0.2 | SC |
| G6 | 15 | 9 | Controls, injected SC with diluent | | | |

*log10 CCID50 per bird

Monitoring: Mortality follow-up, D0 to D21. Weighing at D0 (group randomisation), D10 and D21. Sexing and necropsy for lesions of Derzsy's disease at D21. Blood sampling at D21 and search for duck parvovirus (GM) and Derzsy's (H) antibodies by SN.

Mortality follow-up and post-mortem observations: There were no deaths in any group all through the study. No duck showed any organ lesions at D21 necropsy examination.

Figure 10:
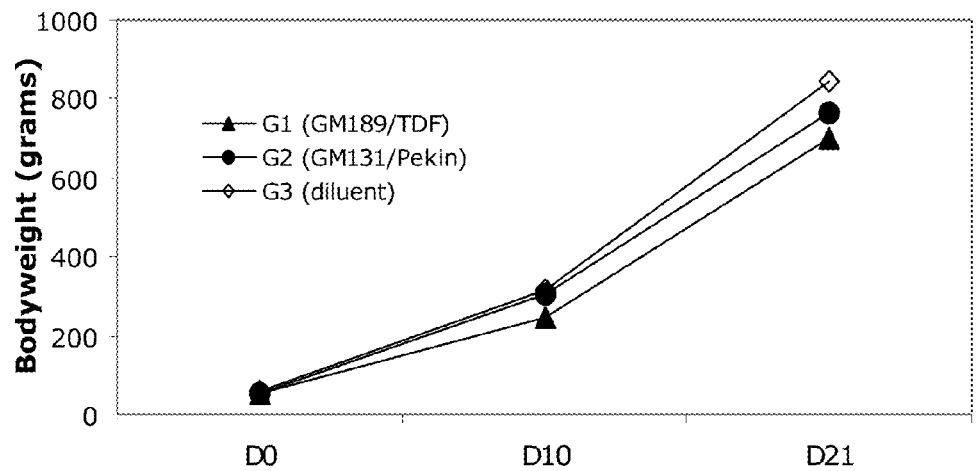
FIG. 10 shows body weight data for ducklings aged 1 day at D0 tested with strain GM131/Pekin and for ducklings tested with strain GM189/TDF.

Weighing results (individual data are given in Table 22 below): G1, G2, G3: Ducks injected at one day of age (see FIG. 10 and Table 18). There was a clear difference between inoculated groups (whatever the strain) and the controls. Table 18 shows mean (m) and standard deviations ($\Phi$). Ducks aged 1 day at D0.

TABLE 18

| Group | | D0 % | D0 & | D10 % | D10 & | D21 % | D21 & |
|---|---|---|---|---|---|---|---|
| G1 | n | 9 | 2 | 9 | 2 | 9 | 2 |
| (GM189/TDF) | m | 55 | 53 | 245 | 242 | 720 | 625 |
| | $\Phi$ | 5.1 | 4.2 | 28.4 | 12.7 | 65.6 | 41.7 |
| G2 | n | 9 | 2 | 9 | 2 | 9 | 2 |
| (GM131/Pekin) | m | 56 | 57 | 303 | 300 | 777 | 697 |
| | $\Phi$ | 7.5 | 4.9 | 41.6 | 9.9 | 76.9 | 29.0 |
| G3 | n | 10 | 1 | 10 | 1 | 10 | 1 |
| (diluent) | m | 60 | 51 | 321 | 265 | 864 | 670 |
| | $\Phi$ | 2.4 | — | 22.2 | — | 47.0 | — |

Figure 11:
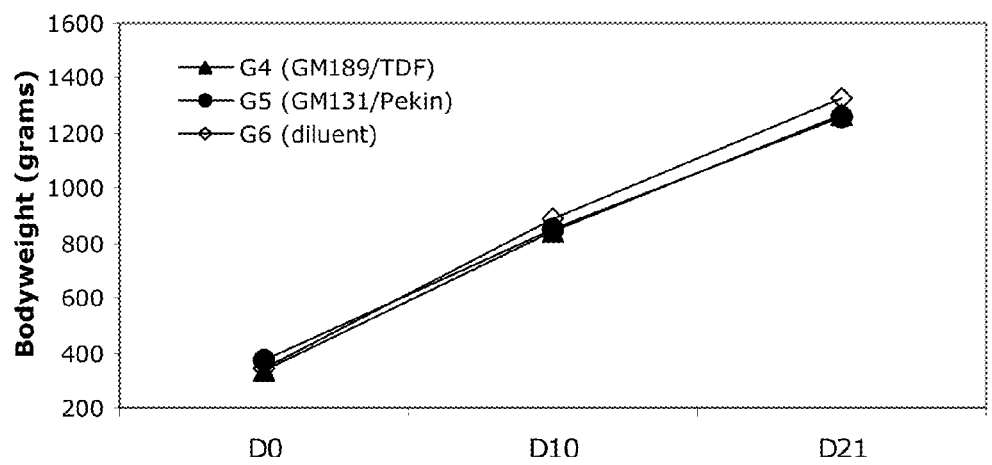
FIG. 11 shows body weight data for ducklings aged 15 days at D0 tested with strain GM131/Pekin and for ducklings tested with strain GM189/TDF.

G4, G5, G6: Ducks injected at 15 days of age (see FIG. 11 and Table 19). Ducks aged 15 days at D0.

TABLE 19

Mean (m) and standard deviations ($\Phi$).

| Group | | D0 % | D0 & | D10 % | D10 & | D21 % | D21 & |
|---|---|---|---|---|---|---|---|
| G4 | n | 2 | 8 | 2 | 8 | 2 | 8 |
| (GM189/TDF) | m | 355 | 335 | 905 | 826 | 1432 | 1228 |
| | $\Phi$ | 145.7 | 39.6 | 295.6 | 65.9 | 356.4 | 66.4 |
| G5 | n | 3 | 7 | 3 | 7 | 3 | 7 |
| (GM131/Pekin) | m | 451 | 336 | 1052 | 769 | 1528 | 1149 |
| | $\Phi$ | 66.7 | 56.2 | 115.4 | 78.1 | 130.2 | 90.7 |
| G6 | n | 3 | 6 | 3 | 6 | 3 | 6 |
| (diluent) | m | 380 | 324 | 1035 | 821 | 1607 | 1191 |
| | $\Phi$ | 17.8 | 46.9 | 18.8 | 94.2 | 66.8 | 90.7 |

The results observed with GM189/TDF and GM131/Pekin were very close to each other. There was no significant differences between the observations in the 3 groups (Multifactor ANOVA on bodyweights, factors group and sex—D0: p=0.19; D10: p=0.49; D21: p=0.44).

Serology results for GM antibodies (Table 20) and H antibodies (Table 21) at D21 are summarized below. Positive reference serum: 2.8 log 10 SN unit (Table 20) and ≥4.0 log 10 SN unit (Table 21).

TABLE 20

| | | SN Titres | |
|---|---|---|---|
| Group | Treatment | Mean SN value (log10) | Range of values |
| G1 | 5.0 log10 CCID50 of GM189/TDF at one-day-old | 2.7 | 2.2-3.4 log10 |
| G2 | 5.0 log10 CCID50 of GM131/Pekin at one-day-old | 1.4 | 1.0-1.6 |
| G3 | Diluent-injected controls for G1/G2 | ≤0.4 | All ≤0.4 |
| G4 | 5.0 log10 CCID50 of GM189/TDF at one-day-old | 2.6 | 2.2-2.8 log10 |
| G5 | 5.0 log10 CCID50 of GM131/Pekin at one-day-old | 1.1 | 1.0-1.6 log10 |
| G6 | Diluent-injected controls for G1/G2 | ≤0.4 | All ≤0.4 |

TABLE 21

| | | SN Titres | |
|---|---|---|---|
| Group | Treatment | Mean SN value (log10) | Range of values |
| G1 | 5.0 log10 CCID50 of GM189/TDF at one-day-old | ≤0.8 [4+/11] | ≤0.4-1.6 log10 |
| G2 | 5.0 log10 CCID50 of GM131/Pekin at one-day-old | ≤0.4 | All ≤0.4 |
| G3 | Diluent-injected controls for G1/G2 | ≤0.4 | All ≤0.4 |
| G4 | 5.0 log10 CCID50 of GM189/TDF at one-day-old | ≤0.9 [8+/11] | ≤0.4-1.6 log10 |
| G5 | 5.0 log10 CCID50 of GM131/Pekin at one-day-old | ≤0.5 [1+/10] | ≤0.4-1.0 log10 |
| G6 | Diluent-injected controls for G1/G2 | ≤0.4 | All ≤0.4 |

The results validated the inoculations. The controls remained seronegative. As expected, the serological conversion obtained with respect to GM antibodies (homologous antibody response) was higher than that regarding H antibodies (heterologous response).

GM serology response was higher in ducks injected with strain GM189/TDF than with GM131/Pekin. The values recorded were similar whatever the age of injection, for each strain type. Mean H serology response was low with the 2 strains used. However, there was a trend to have a serological response in ducks inoculated with strain GM189/TDF, while there was almost no response in birds which received the Pekin-passed strain GM131. The results with respect to H antibodies tended to be better after inoculation of 15-day-old birds.

This study showed that strain GM189/TDF and strain GM131/Pekin were similar from the safety standpoint. Both strains were completely safe with respect to mortality and lesional analysis.

They had no major impact on the birds bodyweight gain when administered at 15 days of age, but induced some growth retardation if inoculated at one day old. In addition, analysis of the serological results indicated that GM189/Pekin induced a better immune response (homologous and heterologous) than strain GM131/Pekin, in particular when administered to 15-day-old ducks.

Table 22 shows individual duck weighing data for Example 11.

According to these studies, the strain finally considered as satisfactorily attenuated was the 189th passage from the initial isolate, obtained as follows: 19 adaptation passages on PDEC (i.e., until GM19); 74 attenuation passages on PDEC (i.e., until GM93); 71 attenuation passages on TDF2A cells at 38° C. (i.e., until GM164) and 25 attenuation passages on TDF2A cells at 33° C. (i.e., until GM189).

FIG. 12 shows a partial nucleotide sequence comparison of the VP1 (viral protein 1) gene between the Palmivax vaccine for GPV (SEQ ID NO. 3) and the invention (i.e., VP1 Parvoduck; SEQ ID NO. 1). The sequences are compared with each other as well as with non-attenuated GPV and MDPV VP1 sequences for homology in Table 23. Protein sequence homology and nucleotide sequence homology (in parentheses) are reported. The GeneBank accession number for the non-attenuated GPV is NC-001701. The GeneBank accession number for the non-attenuated MDPV is NC-006147.

FIG. 13 shows the protein sequence comparison of the VP1 gene between the Palmivax vaccine for GPV (SEQ ID NO. 4) and the invention (i.e., Parvoduck protein sequence; SEQ ID NO. 2).

TABLE 22

| Group | Number | Sex | Bodyweights D0 | D10 | D21 |
| --- | --- | --- | --- | --- | --- |
| G1 (GM189/TDF) | 710 | M | 54 | 223 | 634 |
|  | 714 | M | 53 | 274 | 778 |
|  | 715 | M | 52 | 245 | 761 |
|  | 717 | M | 54 | 255 | 715 |
|  | 718 | M | 56 | 226 | 650 |
|  | 719 | M | 60 | 277 | 798 |
|  | 720 | M | 55 | 250 | 760 |
|  | 721 | M | 65 | 269 | 755 |
|  | 723 | M | 47 | 190 | 630 |
|  | 713 | F | 56 | 233 | 595 |
|  | 716 | F | 50 | 251 | 654 |
| G2 (GM131/Pekin) | 722 | M | 61 | 256 | 837 |
|  | 724 | M | 71 | 360 | 853 |
|  | 725 | M | 54 | 316 | 825 |
|  | 727 | M | 52 | 290 | 761 |
|  | 729 | M | 63 | 372 | 897 |
|  | 730 | M | 50 | 282 | 698 |
|  | 731 | M | 51 | 270 | 718 |
|  | 732 | M | 49 | 319 | 700 |
|  | 733 | M | 52 | 264 | 704 |
|  | 726 | F | 60 | 307 | 717 |
|  | 728 | F | 53 | 293 | 676 |
| G3 (diluent) | 734 | M | 63 | 316 | 859 |
|  | 735 | M | 61 | 328 | 876 |
|  | 736 | M | 60 | 327 | 865 |
|  | 737 | M | 61 | 303 | 828 |
|  | 739 | M | 61 | 329 | 902 |
|  | 740 | M | 63 | 346 | 935 |
|  | 741 | M | 60 | 311 | 826 |
|  | 742 | M | 62 | 349 | 893 |
|  | 743 | M | 55 | 272 | 768 |
|  | 744 | M | 58 | 326 | 885 |
|  | 738 | F | 51 | 265 | 670 |
| G4 (GM189/TDF) | 684 | M | 458 | 1114 | 1684 |
|  | 688 | M | 252 | 696 | 1180 |
|  | 683 | F | 370 | 816 | 1208 |
|  | 685 | F | 294 | 759 | 1142 |
|  | 686 | F | 376 | 873 | 1248 |
|  | 687 | F | 285 | 824 | 1249 |
|  | 689 | F | 326 | 836 | 1245 |
|  | 690 | F | 375 | 887 | 1282 |
|  | 691 | F | 360 | 904 | 1321 |
|  | 692 | F | 295 | 709 | 1126 |
| G5 (GM131/Pekin) | 694 | M | 475 | 1102 | 1632 |
|  | 701 | M | 376 | 920 | 1382 |
|  | 702 | M | 503 | 1134 | 1570 |
|  | 693 | F | 309 | 735 | 1100 |
|  | 695 | F | 332 | 781 | 1175 |
|  | 696 | F | 426 | 890 | 1280 |
|  | 697 | F | 339 | 769 | 1148 |
|  | 698 | F | 312 | 710 | 1074 |
|  | 699 | F | 251 | 658 | 1027 |
|  | 700 | F | 384 | 839 | 1242 |
| G6 (diluent) | 705 | M | 400 | 1046 | 1638 |
|  | 707 | M | 367 | 1013 | 1530 |
|  | 711 | M | 372 | 1045 | 1652 |
|  | 703 | F | 318 | 813 | 1208 |
|  | 704 | F | 311 | 787 | 1126 |
|  | 706 | F | 361 | 857 | 1224 |
|  | 708 | F | 245 | 667 | 1043 |
|  | 709 | F | 330 | 847 | 1290 |
|  | 712 | F | 380 | 953 | 1253 |

TABLE 23

Protein and nucleotide (in parentheses) sequence homology for VP1.

| Comparison | GPV NC-001701 | MDPV NC-006147 | Palmivax | Parvoduck |
| --- | --- | --- | --- | --- |
| GPV NC-001701 | — | 81.5 (87.6) | 97.1 (98.1) | 81.4 (87.6) |
| MDPV NC-006147 | 81.5 (87.6) | — | 81.0 (87.3) | 98.9 (97.5) |
| Palmivax | 97.1 (98.1) | 81.0 (87.3) | — | 81.0 (87.6) |
| Parvoduck | 81.4 (87.6) | 98.9 (97.5) | 81.0 (87.6) | — |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating a palmiped against Muscovy duck parvovirus and goose parvovirus (Derzsy's Disease) or inducing an immunogenic or protective response in an animal against Muscovy duck parvovirus comprising at least one administration of a composition comprising an attenuated palmiped parvovirus, wherein the attenuated palmiped parvovirus comprises a mutated viral protein 1 (VP1) gene, and wherein the attenuated palmiped parvovirus comprises a polynucleotide encoding viral protein 1 (VP1) comprising SEQ ID NO:2.

2. The method of claim 1, wherein the attenuated palmiped parvovirus comprises a polynucleotide comprising SEQ ID NO:1.

3. The method of claim 1 or 2, wherein the composition further comprises an adjuvant.

* * * * *

SEQUENCE LISTING

<160> NUMBER OF SEQ ID NOS: 4

<210> SEQ ID NO 1
<211> LENGTH: 2150
<212> TYPE: DNA
<213> ORGANISM: artificial sequence
<220> FEATURE:
<223> OTHER INFORMATION: VP1 parvoduck DNA

<400> SEQUENCE: 1

```
atgtctaatt ttttagagga atttgaagac tggtatgaga ctgcagccgc atcttggcgg      60
catttgaaag ctggagcccc caagccaaaa tcaaaccagc aatctcagtc tgtgtctaca     120
gacagaaaac ctcaacgaaa agacaataat aggggctttg tacttcctgg ctataagtat     180
cttgggcctg gtaacggcct tgataaaggg ccacctgtca ataaagcgga caacgtcgcg     240
cttgagcacg ataaagcgta cgaccagcag ctcaaggcag gagacaaccc ctatataaaa     300
tttaatcacg cagatcaaga atttatagat aatctgcaag gtgatacctc ctttggaggc     360
aacctcggaa aagccgtatt ccaagctaaa aaagaattc tagagccttt aggcctagta      420
gaagaacctg taaacacggc tcctgctaaa aagagtagtg aaaaactaac agatcactac     480
cctatagtaa agaagcctaa attatctgaa gaaaactctc cttcacgtag taatagtgga     540
ggagaagcaa gtgcagctgc caccgaaggc tccgaacctg tggcagcacc taacatggca     600
gagggaggaa gcggagctat gggcgactct gcaggggtg ccgatggact gggtaatgcc      660
tcaggaaatt ggcattgcga ttcccaatgg ctgggagaca cagtcattac caagactaca     720
agaacctggg tcctgccaag ctacaacaac cacatctaca aagccatcac aagcggaaca     780
aacccagact caaataccca atatgctgga tacagcaccc cctgggggta ctttgatttc     840
aacagattcc actgccattt ctctccaaga cactggcaga gactcatcaa caaccattgg     900
gggattagac cgaaagcact caaattcaag atattcaatg tgcaagttaa gaagttacg     960
acgcaagacc agacaaagac tattgctaac aaccttacct ctacaatcca gatattcacg    1020
gataatgaac accagctgcc ctatgttctg ggctcggcca cggaggggac gatgccaccg    1080
ttcccctcag atgtgtatgc cttgccccag tacggctact gcacaatgca caccaaccag    1140
agtggagcga gattcaatga cagaagtgcc ttctattgct tagagtactt ccccagtcag    1200
atgctgagaa cagggaataa ttttgaattc agttttgagt ttgaagaagt tccttttccat   1260
agcatgttcg ctcattcaca ggatttagac aggctaatga atcctctcct agatcagtac    1320
ctgtggaatt tctctgaggt taatggtggc aggaatgcac agttcaaaaa agctgtgaaa    1380
ggagcatttg gtgcaatggg gagaaattgg cttccaggac ccaaacttct agaccaaagg    1440
gtaagagcat acagtggagg aacagataac tatgcgaact ggtcaatctg gagtaaagga    1500
aacaaagttt ttcttaaaga cagagagtat ctcctgcaac aggtccagt agctactaca     1560
catacagaag atcaggcttc cagtgtaccg gctcaaaaca taataggaat tgcaaaagac    1620
ccctacaggt caggcagtac tctggcagga atttcagaca tcatggtaac agatgagcaa    1680
gaaatagcac caactaacgg tgtagggtgg agaccttatg gattgaccgt aaccaatgaa    1740
caaaacacaa caacagctcc tacaaacgat gagctacaag tactgggagt actacctggc    1800
atggtctggc agaacagaga tatttacctg cagggtccta tatgggctaa ataccccaa     1860
acagatggga aatttcatcc ttctccaaac ctgggaggtt ttggtctcca taatccacct    1920
ccccaggtct tgttaaaaaa tactcctgtt cctgcagatc ctccactaga gtatgtaaat    1980
cagaagtgga attcttacat tacacagtat tcaacagggc agtgtactgt agaaatggtc    2040
tgggaactca gaaaagaaaa ctccaagaga tggaaccctg agatccaatt taccagtaaa    2100
tttggaaata gaacaagtac tatgtttgct ccaaatgaga ctggaggcta              2150
```

```
<210> SEQ ID NO 2
<211> LENGTH: 732
<212> TYPE: PRT
<213> ORGANISM: artificial sequence
<220> FEATURE:
<223> OTHER INFORMATION: VP1 parvoduck protein
```

<400> SEQUENCE: 2

```
Met Ser Asn Phe Leu Glu Glu Phe Glu Asp Trp Tyr Glu Thr Ala Ala
1               5                   10                  15

Ala Ser Trp Arg His Leu Lys Ala Gly Ala Pro Lys Pro Lys Ser Asn
            20                  25                  30

Gln Gln Ser Gln Ser Val Ser Thr Asp Arg Lys Pro Gln Arg Lys Asp
                35                  40                  45

Asn Asn Arg Gly Phe Val Leu Pro Gly Tyr Lys Tyr Leu Gly Pro Gly
50                  55                  60

Asn Gly Leu Asp Lys Gly Pro Pro Val Asn Lys Ala Asp Asn Val Ala
65                  70                  75                  80

Leu Glu His Asp Lys Ala Tyr Asp Gln Gln Leu Lys Ala Gly Asp Asn
                85                  90                  95

Pro Tyr Ile Lys Phe Asn His Ala Asp Gln Glu Phe Ile Asp Asn Leu
                100                 105                 110

Gln Gly Asp Thr Ser Phe Gly Gly Asn Leu Gly Lys Ala Val Phe Gln
            115                 120                 125

Ala Lys Lys Arg Ile Leu Glu Pro Leu Gly Leu Val Glu Glu Pro Val
130                 135                 140

Asn Thr Ala Pro Ala Lys Lys Ser Ser Gly Lys Leu Thr Asp His Tyr
145                 150                 155                 160

Pro Ile Val Lys Lys Pro Lys Leu Ser Glu Asn Ser Pro Ser Arg
                165                 170                 175

Ser Asn Ser Gly Gly Glu Ala Ser Ala Ala Thr Glu Gly Ser Glu
            180                 185                 190

Pro Val Ala Ala Pro Asn Met Ala Glu Gly Gly Ser Gly Ala Met Gly
            195                 200                 205

Asp Ser Ala Gly Gly Ala Asp Gly Leu Gly Asn Ala Ser Gly Asn Trp
210                 215                 220

His Cys Asp Ser Gln Trp Leu Gly Asp Thr Val Ile Thr Lys Thr Thr
225                 230                 235                 240

Arg Thr Trp Val Leu Pro Ser Tyr Asn Asn His Ile Tyr Lys Ala Ile
                245                 250                 255

Thr Ser Gly Thr Asn Pro Asp Ser Asn Thr Gln Tyr Ala Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn His Trp Gly Ile Arg Pro
            290                 295                 300

Lys Ala Leu Lys Phe Lys Ile Phe Asn Val Gln Val Lys Glu Val Thr
305                 310                 315                 320

Thr Gln Asp Gln Thr Lys Thr Ile Ala Asn Asn Leu Thr Ser Thr Ile
                325                 330                 335

Gln Ile Phe Thr Asp Asn Glu His Gln Leu Pro Tyr Val Leu Gly Ser
                340                 345                 350

Ala Thr Glu Gly Thr Met Pro Pro Phe Pro Ser Asp Val Tyr Ala Leu
            355                 360                 365

Pro Gln Tyr Gly Tyr Cys Thr Met His Thr Asn Gln Ser Gly Ala Arg
            370                 375                 380

Phe Asn Asp Arg Ser Ala Phe Tyr Cys Leu Glu Tyr Phe Pro Ser Gln
385                 390                 395                 400

Met Leu Arg Thr Gly Asn Asn Phe Glu Phe Ser Phe Glu Phe Glu Glu
```

```
                    405                 410                 415
Val Pro Phe His Ser Met Phe Ala His Ser Gln Asp Leu Asp Arg Leu
                420                 425                 430

Met Asn Pro Leu Leu Asp Gln Tyr Leu Trp Asn Phe Ser Glu Val Asn
            435                 440                 445

Gly Gly Arg Asn Ala Gln Phe Lys Lys Ala Val Lys Gly Ala Phe Gly
        450                 455                 460

Ala Met Gly Arg Asn Trp Leu Pro Gly Pro Lys Leu Leu Asp Gln Arg
465                 470                 475                 480

Val Arg Ala Tyr Ser Gly Gly Thr Asp Asn Tyr Ala Asn Trp Ser Ile
                485                 490                 495

Trp Ser Lys Gly Asn Lys Val Phe Leu Lys Asp Arg Glu Tyr Leu Leu
                500                 505                 510

Gln Pro Gly Pro Val Ala Thr Thr His Thr Glu Asp Gln Ala Ser Ser
            515                 520                 525

Val Pro Ala Gln Asn Ile Ile Gly Ile Ala Lys Asp Pro Tyr Arg Ser
        530                 535                 540

Gly Ser Thr Leu Ala Gly Ile Ser Asp Ile Met Val Thr Asp Glu Gln
545                 550                 555                 560

Glu Ile Ala Pro Thr Asn Gly Val Gly Trp Arg Pro Tyr Gly Leu Thr
                565                 570                 575

Val Thr Asn Glu Gln Asn Thr Thr Thr Ala Pro Thr Asn Asp Glu Leu
            580                 585                 590

Gln Val Leu Gly Val Leu Pro Gly Met Val Trp Gln Asn Arg Asp Ile
        595                 600                 605

Tyr Leu Gln Gly Pro Ile Trp Ala Lys Ile Pro Gln Thr Asp Gly Lys
    610                 615                 620

Phe His Pro Ser Pro Asn Leu Gly Gly Phe Gly Leu His Asn Pro Pro
625                 630                 635                 640

Pro Gln Val Phe Val Lys Asn Thr Pro Val Pro Ala Asp Pro Pro Leu
                645                 650                 655

Glu Tyr Val Asn Gln Lys Trp Asn Ser Tyr Ile Thr Gln Tyr Ser Thr
            660                 665                 670

Gly Gln Cys Thr Val Glu Met Val Trp Glu Leu Arg Lys Glu Asn Ser
        675                 680                 685

Lys Arg Trp Asn Pro Glu Ile Gln Phe Thr Ser Lys Phe Gly Asn Arg
    690                 695                 700

Thr Ser Thr Met Phe Ala Pro Asn Glu Thr Gly Gly Tyr Val Glu Asp
705                 710                 715                 720

Arg Leu Ile Gly Thr Arg Tyr Leu Thr Gln Asn Leu
                725                 730

<210> SEQ ID NO 3
<211> LENGTH: 2150
<212> TYPE: DNA
<213> ORGANISM: artificial sequence
<220> FEATURE:
<223> OTHER INFORMATION: VP1 Palmivax DNA

<400> SEQUENCE: 3
atgtctactt ttttagattc ttttgaagag tggtatgaga ctgcagccgc ctcgtggcgg      60
aatctgaaag ctggagcccc tcagccaaaa ccaaaccagc agtctcagtc tgtgtctcca     120
gacagagaac ccgaaggaaa agataataat cggggctttg tacttcctgg ctataagtat     180
cttgggcctg gtaacggtct tgataaaggc ccacctgtca ataaggcgga caacgtcgcg     240
```

```
cttgaacacg acaaggccta cgacctacag cttaaagcgg agacaatccc atatataaaa    300
ttcaatcacg ctgaccagga ctttatagat agcctccaag acgaccactc atttggaggt    360
aatcttggaa aggctgtatt ccaggccaaa aaacgtatct tagagccatt cggcctagta    420
gaagagccta tcaacacggc acctgcaaaa aaaatacagg gaagcttac tgaccattac     480
ccagtagtta agaagcctaa actcaccgag gaagtcagtg cgggaggtgg tagcagtgcc    540
gtacaagacg gaggagccac cgcggagggc accgaacctg tggcagcatc tgaaatggca    600
gagggaggag gcggagctat gggcgactct caggggggtg ccgatggagt gggtaatgcc    660
tcgggaaatt ggcattgcga ttcccaatgg atgggaaaca cagtcatcac aaagaccacc    720
agaacctggg tcctgccaag ctacaacaat cacatctaca aagcaattac cagtggaacc    780
tctcaagatg caaatgtcca gtatgctgga tacagtaccc cctgggggta ctttgatttc    840
aatcgcttcc actgccactt ctcccctaga gactggcaga gacttatcaa caaccactgg    900
ggaatcaggc ccaagtctct taaattcaag atcttcaatg ttcaagtcaa ggaagtcaca    960
acgcaggatc agacaaagac cattgcaaac aatctcacct caacaattca gttttttacg   1020
gatgatgagc atcaactccc gtatgtcctg ggctcggcta cggaagggac catgccgccg   1080
ttcccgtcgg atgtctatgc cctgccgcag tacgggtact gcacaatgca caccaaccag   1140
aatggagcac ggttcaatga ccgtagtgca ttctactgct tagagtactt ccctagtcag   1200
atgctgagaa caggtaacaa ctttgagttc acatttgact ttgaagaagt tccttttccac  1260
agcatgttcg ctcattcaca ggacttagac aggcttatga ccccctagt ggatcaatac    1320
ctctggaatt tcaatgaggt agacagcagc agaaatgctc aatttaaaaa agctgtgaaa   1380
ggggcttatg gcaccatggg ccgcaattgg ctgccaggac ctaaattcct ggatcagaga   1440
gttagggcct acccaggagg aacagacaat tatgcaaact ggaacatctg gagtaatggg   1500
aacaaggtga atttaaagga caggcagtat ctcctacaac ccggacctgt gtcagctact   1560
cacacagaaa gggaggcttc cagcatccca gctcagaata ttttagggat agctaaagat   1620
ccatacagat ctggcagcac tacagcagga ataagtgata ttatggtcac ggacgagcag   1680
gaagtagcac ccacaaatgt agtagggtgg aaaccatatg gtaggactgt aacgaatgaa   1740
caaaacacta ctacagctcc tacaagttca gatctggatg ttcttggagc tttaccagga   1800
atggtgtggc agaacagaga tatatatctg cagggaccta tttgggcaaa aataccgaag   1860
actgatggca aattccatcc ttctccaaat ctcggaggat ttggcctgca caatccacca   1920
ccacaggtct tcatcaagaa taccagta cctgcagacc ctccagtaga atatgtgcac    1980
cagaagtgga actcctacat aactcagtac tctacgggcc agtgtacagt agaaatggtg   2040
tgggagctga aaagagaa ttcaaagaga tggaacccag aaatccagtt caccagcaat     2100
ttcagtaaca gaacaaacat aatgtttgca cctaatgaaa ctggtggata             2150
```

<210> SEQ ID NO 4
<211> LENGTH: 732
<212> TYPE: PRT
<213> ORGANISM: artificial sequence
<220> FEATURE:
<223> OTHER INFORMATION: VP1 Palmivax protein

<400> SEQUENCE: 4

Met Ser Thr Phe Leu Asp Ser Phe Glu Glu Trp Tyr Glu Thr Ala Ala
1               5                   10                  15

Ala Ser Trp Arg Asn Leu Lys Ala Gly Ala Pro Gln Pro Lys Pro Asn

```
            20                  25                  30
Gln Gln Ser Gln Ser Val Ser Pro Asp Arg Glu Pro Glu Gly Lys Asp
        35                  40                  45
Asn Asn Arg Gly Phe Val Leu Pro Gly Tyr Lys Tyr Leu Gly Pro Gly
    50                  55                  60
Asn Gly Leu Asp Lys Gly Pro Val Asn Lys Ala Asp Asn Val Ala
65                  70                  75                  80
Leu Glu His Asp Lys Ala Tyr Asp Leu Gln Leu Lys Ala Gly Asp Asn
                85                  90                  95
Pro Tyr Ile Lys Phe Asn His Ala Asp Gln Asp Phe Ile Asp Ser Leu
            100                 105                 110
Gln Asp Asp His Ser Phe Gly Gly Asn Leu Gly Lys Ala Val Phe Gln
            115                 120                 125
Ala Lys Lys Arg Ile Leu Glu Pro Phe Gly Leu Val Glu Glu Pro Ile
            130                 135                 140
Asn Thr Ala Pro Ala Lys Lys Asn Thr Gly Lys Leu Thr Asp His Tyr
145                 150                 155                 160
Pro Val Val Lys Lys Pro Lys Leu Thr Glu Glu Val Ser Ala Gly Gly
                165                 170                 175
Gly Ser Ser Ala Val Gln Asp Gly Gly Ala Thr Ala Glu Gly Thr Glu
            180                 185                 190
Pro Val Ala Ala Ser Glu Met Ala Glu Gly Gly Gly Ala Met Gly
            195                 200                 205
Asp Ser Ser Gly Gly Ala Asp Gly Val Gly Asn Ala Ser Gly Asn Trp
    210                 215                 220
His Cys Asp Ser Gln Trp Met Gly Asn Thr Val Ile Thr Lys Thr Thr
225                 230                 235                 240
Arg Thr Trp Val Leu Pro Ser Tyr Asn Asn His Ile Tyr Lys Ala Ile
                245                 250                 255
Thr Ser Gly Thr Ser Gln Asp Ala Asn Val Gln Tyr Ala Gly Tyr Ser
            260                 265                 270
Thr Pro Trp Gly Tyr Phe Asp Phe Asn Arg Phe His Cys His Phe Ser
            275                 280                 285
Pro Arg Asp Trp Gln Arg Leu Ile Asn Asn His Trp Gly Ile Arg Pro
        290                 295                 300
Lys Ser Leu Lys Phe Lys Ile Phe Asn Val Gln Val Lys Glu Val Thr
305                 310                 315                 320
Thr Gln Asp Gln Thr Lys Thr Ile Ala Asn Asn Leu Thr Ser Thr Ile
                325                 330                 335
Gln Val Phe Thr Asp Asp Glu His Gln Leu Pro Tyr Val Leu Gly Ser
            340                 345                 350
Ala Thr Glu Gly Thr Met Pro Pro Phe Pro Ser Asp Val Tyr Ala Leu
            355                 360                 365
Pro Gln Tyr Gly Tyr Cys Thr Met His Thr Asn Gln Asn Gly Ala Arg
        370                 375                 380
Phe Asn Asp Arg Ser Ala Phe Tyr Cys Leu Glu Tyr Phe Pro Ser Gln
385                 390                 395                 400
Met Leu Arg Thr Gly Asn Asn Phe Glu Phe Thr Phe Asp Phe Glu Glu
                405                 410                 415
Val Pro Phe His Ser Met Phe Ala His Ser Gln Asp Leu Asp Arg Leu
            420                 425                 430
Met Asn Pro Leu Val Asp Gln Tyr Leu Trp Asn Phe Asn Glu Val Asp
        435                 440                 445
```

-continued

```
Ser Ser Arg Asn Ala Gln Phe Lys Lys Ala Val Lys Gly Ala Tyr Gly
    450             455             460

Thr Met Gly Arg Asn Trp Leu Pro Gly Pro Lys Phe Leu Asp Gln Arg
465             470             475             480

Val Arg Ala Tyr Pro Gly Gly Thr Asp Asn Tyr Ala Asn Trp Asn Ile
            485             490             495

Trp Ser Asn Gly Asn Lys Val Asn Leu Lys Asp Arg Gln Tyr Leu Leu
            500             505             510

Gln Pro Gly Pro Val Ser Ala Thr His Thr Glu Arg Glu Ala Ser Ser
        515             520             525

Ile Pro Ala Gln Asn Ile Leu Gly Ile Ala Lys Asp Pro Tyr Arg Ser
    530             535             540

Gly Ser Thr Thr Ala Gly Ile Ser Asp Ile Met Val Thr Asp Glu Gln
545             550             555             560

Glu Val Ala Pro Thr Asn Val Val Gly Trp Lys Pro Tyr Gly Arg Thr
            565             570             575

Val Thr Asn Glu Gln Asn Thr Thr Thr Ala Pro Thr Ser Ser Asp Leu
            580             585             590

Asp Val Leu Gly Ala Leu Pro Gly Met Val Trp Gln Asn Arg Asp Ile
        595             600             605

Tyr Leu Gln Gly Pro Ile Trp Ala Lys Ile Pro Lys Thr Asp Gly Lys
    610             615             620

Phe His Pro Ser Pro Asn Leu Gly Gly Phe Gly Leu His Asn Pro Pro
625             630             635             640

Pro Gln Val Phe Ile Lys Asn Thr Pro Val Pro Ala Asp Pro Pro Val
            645             650             655

Glu Tyr Val His Gln Lys Trp Asn Ser Tyr Ile Thr Gln Tyr Ser Thr
            660             665             670

Gly Gln Cys Thr Val Glu Met Val Trp Glu Leu Arg Lys Glu Asn Ser
        675             680             685

Lys Arg Trp Asn Pro Glu Ile Gln Phe Thr Ser Asn Phe Ser Asn Arg
    690             695             700

Thr Asn Ile Met Phe Ala Pro Asn Glu Thr Gly Gly Tyr Val Glu Asp
705             710             715             720

Arg Leu Ile Gly Thr Arg Tyr Leu Thr Gln Asn Leu
            725             730
```